US012318315B2

(12) United States Patent
Norman et al.

(10) Patent No.: US 12,318,315 B2
(45) Date of Patent: Jun. 3, 2025

(54) DECODING MOVEMENT INTENTION USING ULTRASOUND NEUROIMAGING

(71) Applicants: California Institute of Technology, Pasadena, CA (US); INSERM (Institut National de la Santé et de la Recherche Médicale), Paris (FR); CNRS-CENTRE NATIONAL DE LA RECHERCHE SCIENTIFIQUE, Paris (FR); Ecole Supérieure de Physique et de Chimie Industrielles de la Ville de Paris, Paris (FR)

(72) Inventors: Sumner L Norman, Pasadena, CA (US); David Maresca, Pasadena, CA (US); Vasileios Christopoulos, Riverside, CA (US); Mikhail Shapiro, Pasadena, CA (US); Richard A Andersen, Pasadena, CA (US); Mickael Tanter, Paris (FR); Charlie Demene, Paris (FR)

(73) Assignees: California Institute of Technology, Pasdena, CA (US); INSERM (Institut National de la Santé et de la Recherche Médicale), Paris (FR); CNRS-CENTRE NATIONAL DE LA RECHERCHE SCIENTIFIQUE, Paris (FR); Ecole Supérieure de Physique et de Chimie Industrielles de la Ville de Paris, Paris (FR)

( * ) Notice: Subject to any disclaimer, the term of this patent is extended or adjusted under 35 U.S.C. 154(b) by 933 days.

(21) Appl. No.: 17/318,821

(22) Filed: May 12, 2021

(65) Prior Publication Data

US 2021/0353439 A1   Nov. 18, 2021

Related U.S. Application Data

(60) Provisional application No. 63/023,453, filed on May 12, 2020.

(51) Int. Cl.
  *A61B 8/06*    (2006.01)
  *A61F 2/70*   (2006.01)
  (Continued)

(52) U.S. Cl.
  CPC .................. *A61F 2/70* (2013.01); *A61B 8/06* (2013.01); *A61F 4/00* (2013.01); *A61N 1/08* (2013.01);
  (Continued)

(58) Field of Classification Search
  CPC .......... A61B 8/06; A61B 8/485; A61B 8/486; A61B 8/488; A61B 8/0808; A61B 8/483
  See application file for complete search history.

(56) References Cited

U.S. PATENT DOCUMENTS 9,486,332 B2   11/2016   Harshbarger et al.
9,566,174 B1    2/2017   De Sapio et al.
(Continued)

FOREIGN PATENT DOCUMENTS

KR   10-2019-0073214 A   6/2019
WO      2014142962 A1   9/2014
(Continued)

OTHER PUBLICATIONS

ISR and WO for PCT/US2021/032041 dated Aug. 31, 2021, 9 pages.
ISR and WO for PCT/US2023/071697 dated Nov. 22, 2023, 12 pages.
ISR and WO for PCT/US2023/079245 dated Apr. 15, 2024, 10 pages.

*Primary Examiner* — Baisakhi Roy
(74) *Attorney, Agent, or Firm* — Nixon Peabody LLP

(57) ABSTRACT

Methods and systems are provided for decoding movement intentions using functional ultrasound (fUS) imaging of the brain. In one example, decoding movement intentions include determining a memory phase of a cognitive state of
(Continued)

the brain, the memory phase between a gaze fixation phase and movement execution phase, and determining one or more movement intentions including one or more of intended effector (e.g., hand, eye) and intended direction (e.g., right, left) according to a machine learning algorithm trained to classify one or more movement intentions simultaneously.

17 Claims, 17 Drawing Sheets

(51) Int. Cl.
    *A61F 4/00*         (2006.01)
    *A61N 1/08*         (2006.01)
    *G06N 20/00*       (2019.01)
    *G16H 30/40*       (2018.01)

(52) U.S. Cl.
    CPC ............. *G06N 20/00* (2019.01); *G16H 30/40* (2018.01); *A61F 2002/704* (2013.01)

(56) References Cited

U.S. PATENT DOCUMENTS

| | | | |
|---|---|---|---|
| 9,824,607 | B1 | 11/2017 | Bhattacharyya et al. |
| 10,441,190 | B2 | 10/2019 | Hill et al. |
| 11,276,001 | B1 | 3/2022 | Sutherland et al. |
| 2005/0228515 | A1 | 10/2005 | Musallam et al. |
| 2009/0221928 | A1* | 9/2009 | Einav .................... A61B 5/4076 601/5 |
| 2010/0191139 | A1 | 7/2010 | Jacquin et al. |
| 2012/0083647 | A1* | 4/2012 | Scheinin .............. A61N 5/0622 607/101 |
| 2013/0197401 | A1* | 8/2013 | Sato ........................ A61N 7/00 601/2 |
| 2014/0343399 | A1 | 11/2014 | Posse |
| 2016/0300352 | A1* | 10/2016 | Raj ....................... G06V 10/764 |
| 2017/0042440 | A1 | 2/2017 | Even-Chen et al. |
| 2017/0325705 | A1* | 11/2017 | Ramos Murguialday ................... A61B 5/486 |
| 2018/0177487 | A1* | 6/2018 | Deffieux .............. A61B 8/0816 |
| 2018/0177619 | A1 | 6/2018 | Zhang et al. |
| 2018/0239430 | A1* | 8/2018 | Tadi ....................... H01L 33/58 |
| 2019/0133550 | A1 | 5/2019 | Liu et al. |
| 2019/0261957 | A1* | 8/2019 | Zaslavsky .............. A61B 8/565 |
| 2021/0041953 | A1* | 2/2021 | Poltorak ................. H04W 4/80 |
| 2024/0046071 | A1 | 2/2024 | Aflalo et al. |

FOREIGN PATENT DOCUMENTS

| | | |
|---|---|---|
| WO | 2021231609 A1 | 11/2021 |
| WO | 2024031064 A1 | 2/2024 |
| WO | 2024102917 A1 | 5/2024 |

* cited by examiner

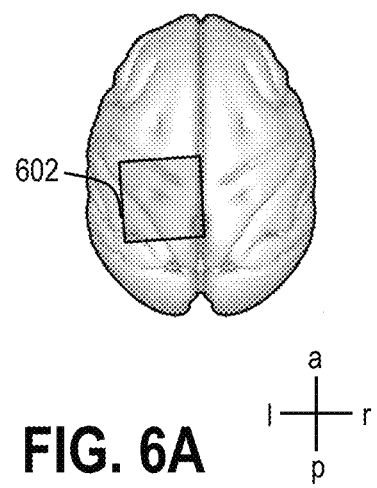
FIG. 6A
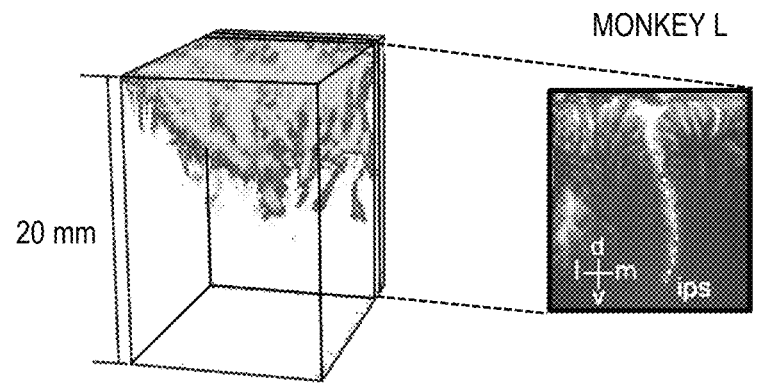
FIG. 6C     FIG. 6E
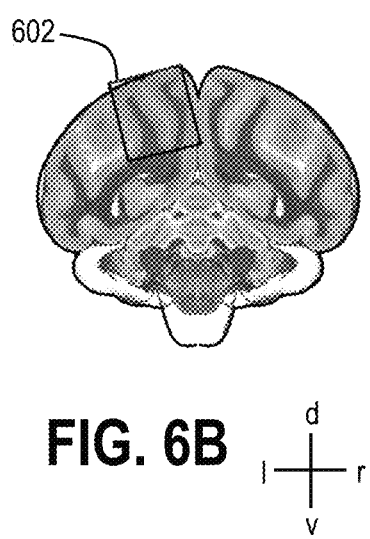
FIG. 6B
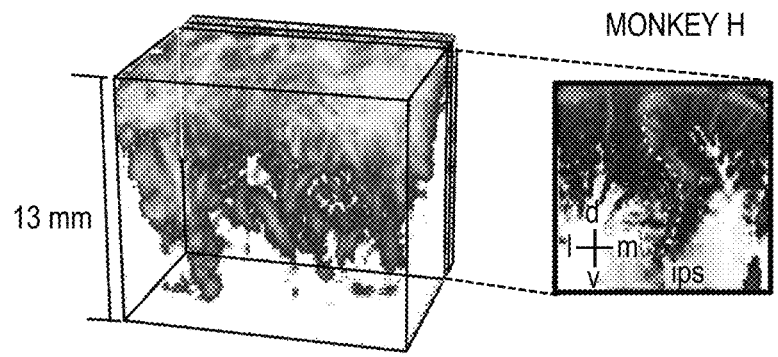
FIG. 6D     FIG. 6F

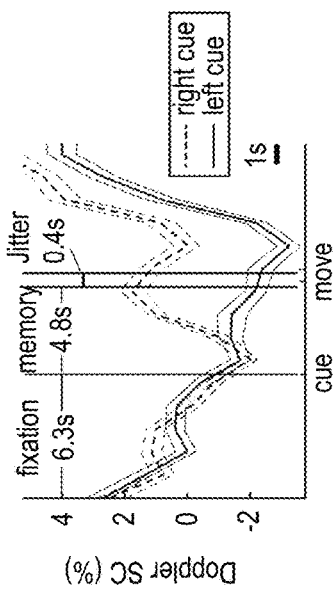
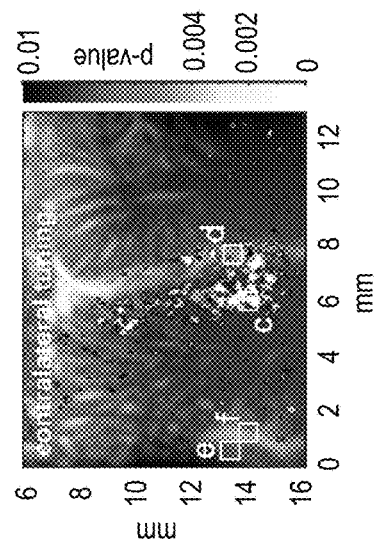
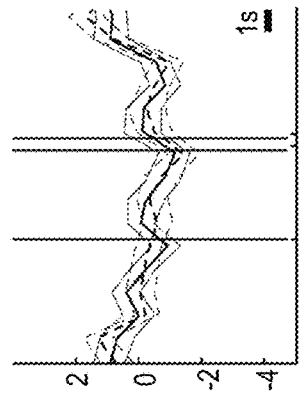
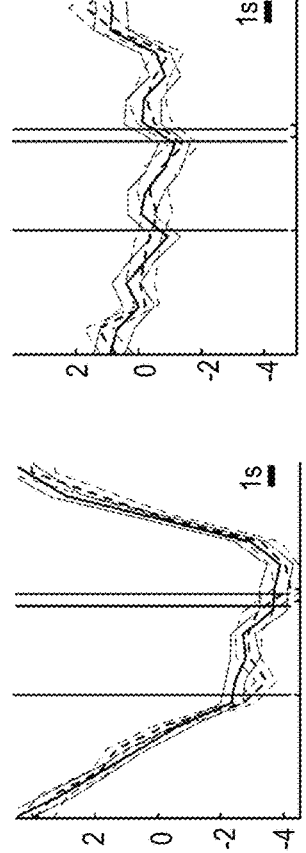
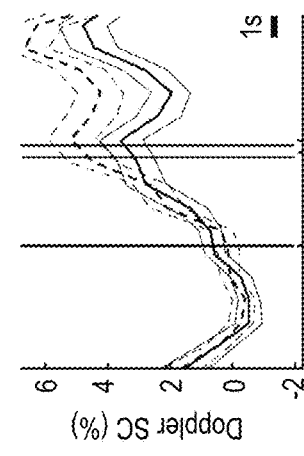
FIG. 7B
FIG. 7C
FIG. 7D
FIG. 7E
FIG. 7F

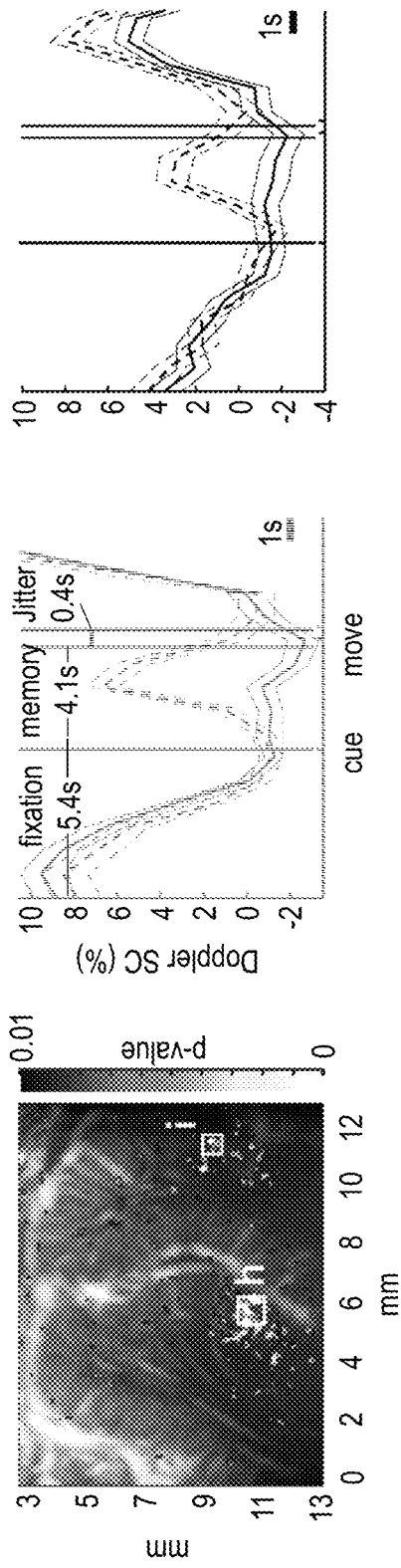
FIG. 7G  FIG. 7H  FIG. 7I

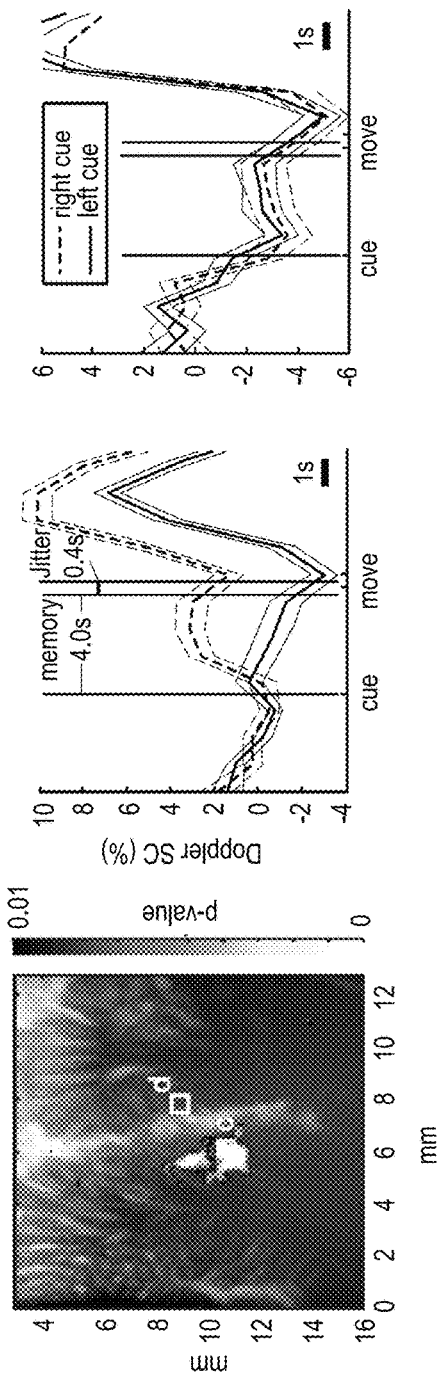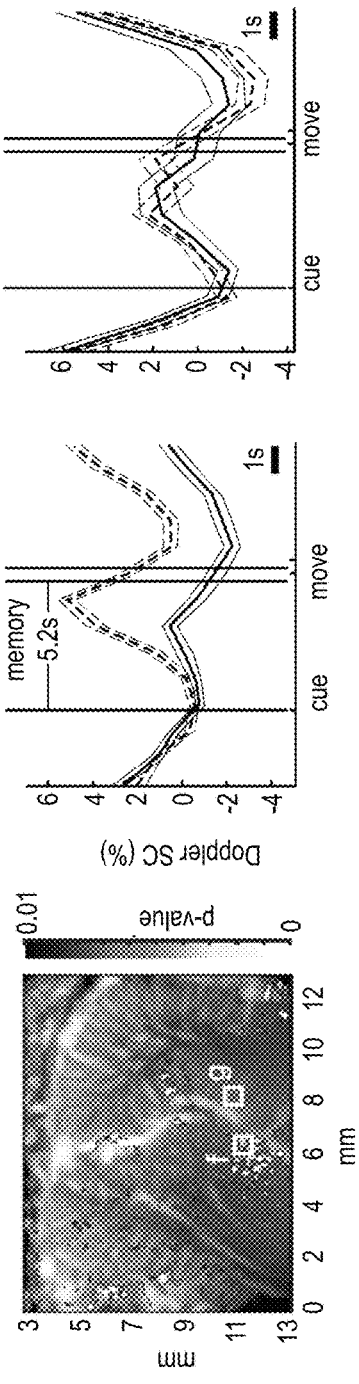

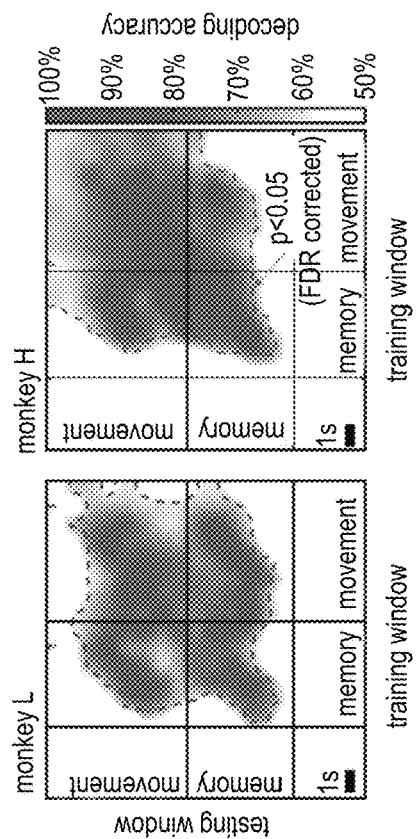
FIG. 9A
FIG. 9B
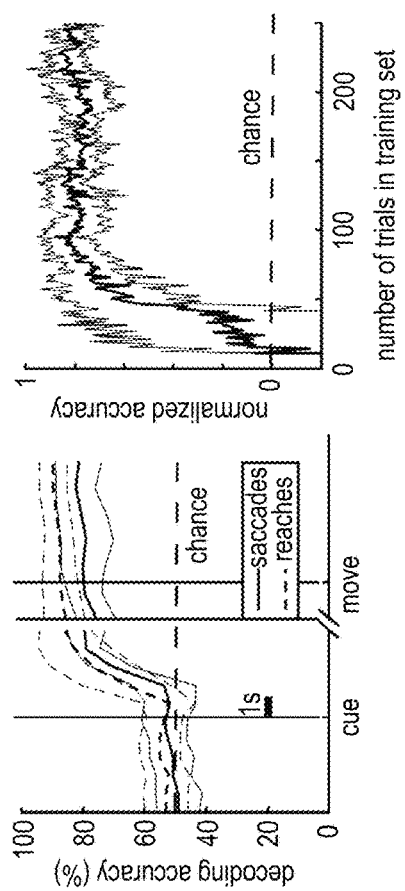
FIG. 9C
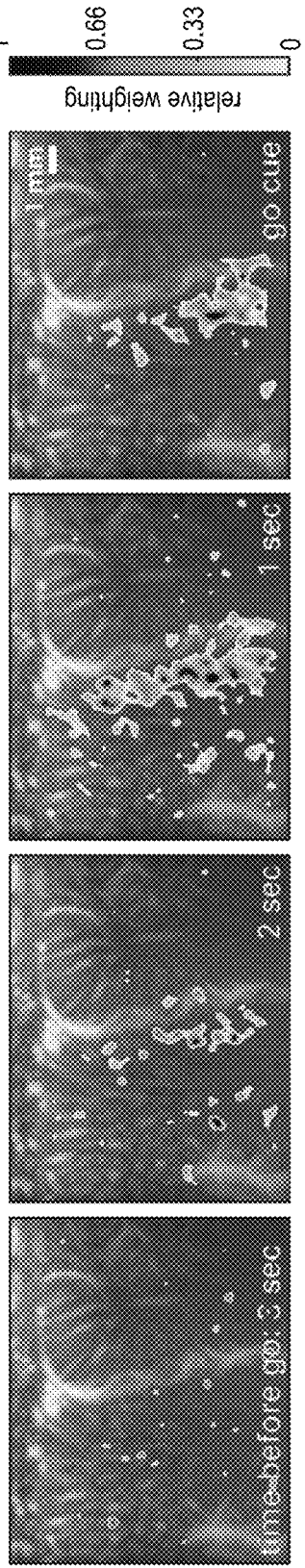
FIG. 9D

DECODING MOVEMENT INTENTION USING ULTRASOUND NEUROIMAGING

CROSS REFERENCE TO RELATED APPLICATIONS

This application claims priority to U.S. Provisional Application No. 63/023,453 filed May 12, 2020 titled "DECODING MOVEMENT INTENTION USING ULTRASOUND NEUROIMAGING", the contents of which are incorporated herein by reference in its entirety.

STATEMENT REGARDING FEDERALLY SPONSORED RESEARCH OR DEVELOPMENT

This invention was made with government support under Grant No. NS099724 awarded by National Institutes of Health. The government has certain rights in the invention.

FIELD

The present invention is directed to movement intention decoding, and more particularly to movement intention decoding using neuroimaging.

BACKGROUND

The following description includes information that may be useful in understanding the present invention. It is not an admission that any of the information provided herein is prior art or relevant to the presently claimed invention, or that any publication specifically or implicitly referenced is prior art.

Technologies for interfacing with the brain are key to understanding the dynamic activity of neural circuits and systems and diagnosing and treating neurological diseases. Many neural interfaces are based on intracortical electrophysiology, which provides direct access to the electrical signals of neurons. However, the electrodes must be implanted via significant-risk open-brain surgery. This process causes acute and chronic local tissue damage and implants suffer material degradation over time. Invasive electrodes are also difficult to scale and limited in sampling density and brain coverage. These factors limit longevity and performance. Noninvasive approaches, such as electroencephalography (EEG) and functional magnetic resonance imaging (fMRI), are limited by low spatial resolution, summing activity of large brain volumes, and the dispersion of signal through various tissues and bone. Minimally invasive techniques such as epidural electrocorticography (ECoG) span a middle ground, maintaining relatively high performance without damaging healthy brain tissue. However, it is difficult to resolve signals from deep cortical or subcortical structures with spatial specificity. In addition, subdural ECoG remains invasive in requiring penetration of the dura and exposure of underlying brain tissue.

SUMMARY

The disclosed technology is directed to improvements in brain-machine interfaces (BMI), that record brain activity to decode motor planning activity that precedes movement. Functional ultrasound (fUS) imaging is used to detect and visualize regional changes in blood flow metrics using Doppler angiography. As an example, these include cerebral blood flow (CBF) and cerebral blood volume (CBV). The benefits of fUS compared to established neuroimaging techniques include substantial increases in spatiotemporal resolution (<100 micron and 100 ms) and sensitivity across a large field of view (several cm).

fUS has been used to image neural activity in rodents, and in non-rodent species, such as ferrets, non-human primates (NIP), and humans. In one example, Dizeux, A et al. in Nature Communications 10, 1400 (2019) titled "Functional ultrasound imaging of the brain reveals propagation of task-related brain activity in behaving primates." show changes in CBV in the supplementary eye field (SEF) during an eye movement task and mapped directional functional connectivity within cortical layers. Dizeux et al. showed that the correlation of fUS signal from SEF and the behavior signal was statistically predictive of the success rate of the animal. However, this prediction required >40 s of data and predicted the success rate of the animal aggregated over the remainder of the recording session.

In another study, Blaize et al. in Proc. Natl. Acad. Sci. USA 117, 14453-14463 (2020) titled "Functional ultrasound imaging of deep visual cortex in awake nonhuman primates." used a binary classification (50% chance level) technique to determine the number of trials necessary to construct retinotopic maps in NHPs. Within an imaging frame, they predicted whether each pixel's activation would change by more than 10% in response to a stimulus with 89% accuracy after 10 averaged trials for one monkey and 91.8% for the second monkey.

The above-mentioned fUS approaches require large amounts of data recorded during multiple trials (at least 40 s or 10 trials) to decode neural activity. Critically, these approaches do not predict behavioral variables (e.g. movement intention) based on data about the neural state of the animal. Further, the above approaches record neural activity during behavior or stimulus rather than activity that precedes the behavior or stimulus. Thus, these approaches are not suitable for implementing in BMIs.

The inventors herein have identified the above-mentioned disadvantages. Further, the inventors have identified that fUS can be used in a portable and minimally invasive manner for neuroimaging and can therefore be applied in BMIs. Accordingly, the inventors provide methods and systems to address the above-mentioned issues in the previous approaches. In one example, a neural interface system comprising: at least one ultrasound transducer; a controller storing instructions in non-transitory memory that when executed cause the controller to: acquire, via the at least one ultrasound transducer, a plurality of functional ultrasound images; process the plurality of functional ultrasound images, in real-time, to determine one or more movement intentions; and adjust one or more actuators of a device, in real-time, according to the one or more movement intentions, the device communicatively coupled to the controller; wherein the at least one ultrasound transducer is positioned to image an area of a brain of a subject.

The inventors herein have identified the sensitivity of fUS to hemodynamic signals as a key advancement that could make fUS-based BMIs possible. By further developing fUS sequences, the inventors show that it is possible to predict, with significant accuracy, the movement intentions of the subject with sufficient sensitivity that only one trial is required ("single-trial decoding").

In addition, the inventors use fUS to decode movement intentions before they are executed or attempted. The inventors show that CBV changes correlate with movement intentions even before a movement is attempted or executed, and that fUS can be used as a BMI to predict movement intentions and control movement of a device.

The inventors herein have identified fUS as a technique for detecting the neural correlates of movement planning from areas in the brain that are involved in sensorimotor integration and movement planning. As one non-limiting example, the inventors identified primary motor cortex and posterior parietal cortex as brain regions from which to record fUS signals for the detection of movement goals and movement planning.

As one non-limiting example, functional ultrasound images can be processed in real-time by a trained decoding algorithm to detect movement intentions during a memory phase of a subject when the subject forms intentions to perform a movement. Thus, by decoding hemodynamic activity, neural activity that correlates with behavior can be detected before the behavior's onset. Further, the trained decoding algorithm applies a linear transformation to fUS images, which enables hemodynamic activity to be decoded on a single-trial basis and due to high resolution and sensitivity of fUS images, the movement intention decoding is achieved with high accuracy.

The systems and methods described herein provide significant advances including but not limited to (1) classification of behavior using fUS data from a single trial, (2) detection of the neural correlates of behavior before its onset, (3) the first investigation of motor planning using fUS, and (4) significant advances in ultrafast ultrasound imaging for single trial and real-time imaging for fUS implementation in BMI.

Further, the methods and systems described herein are technological achievements by introducing minimal latency and being robust across subjects and task paradigms. Thus, the methods and systems described herein can be applied in a range of tasks and applications that benefit from real-time signal detection.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements and are not drawn to scale.

FIGS. 6A-6F show example anatomical scanning regions in non-human primates, according to an embodiment of the disclosure;

FIGS. 7A-7F show an example saccade task, and event related response maps and waveforms during the saccade tasks performed by monkey L, according to an embodiment of the disclosure;

FIGS. 7G-7I show activity map and event-related average waveforms within labeled regions of interest for monkey H, according to an embodiment of the disclosure;

FIGS. 8A-8G show example reach task, event related response map, and waveforms, according to an embodiment of the disclosure;

FIGS. 9A-9D illustrate example single-trial decoding of intended movement direction, according to an embodiment of the disclosure;

Figure 1A:
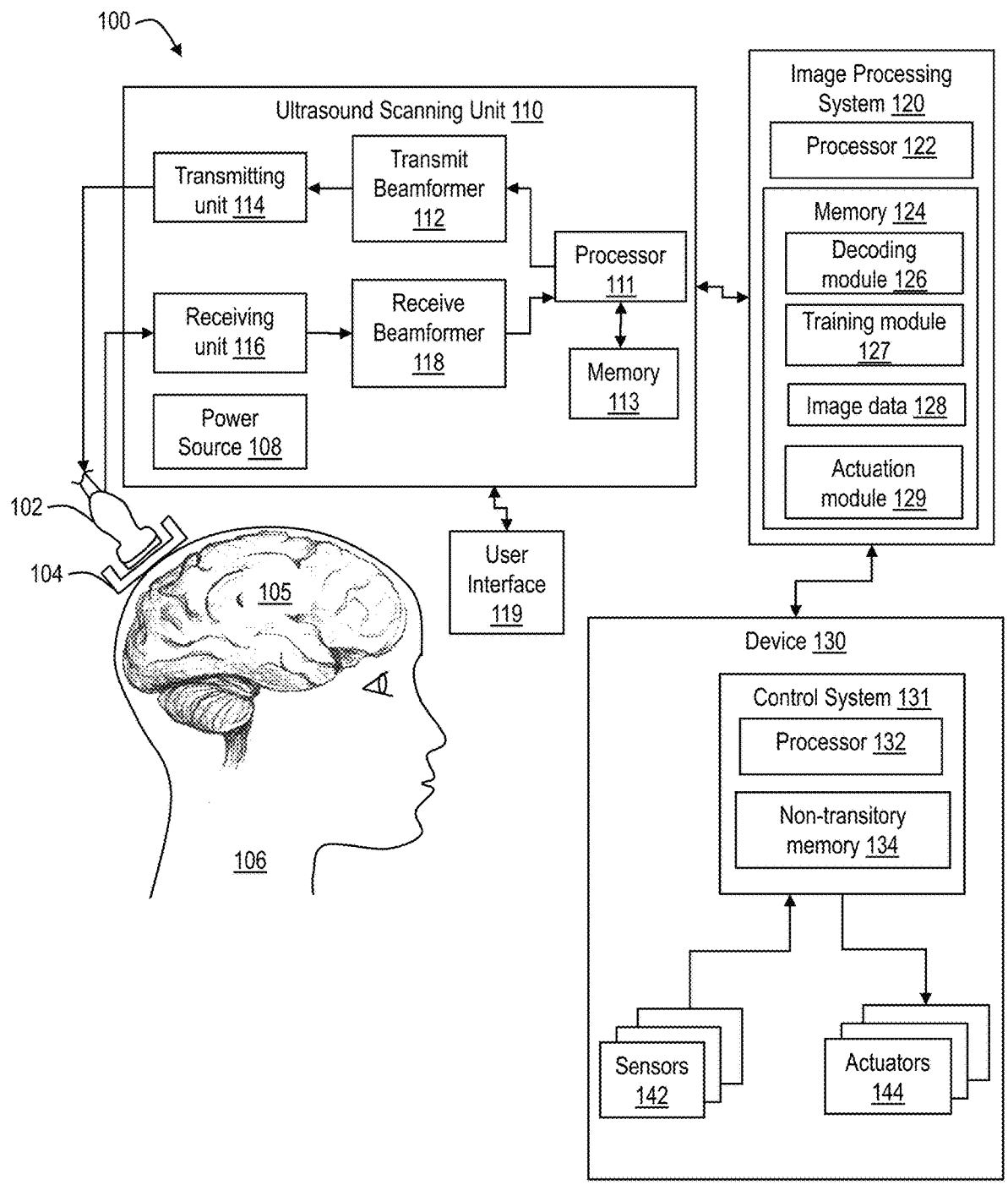
FIG. 1A is a block diagram of a neural interface system for real-time decoding of neural activity using functional ultrasound (fUS), according to an embodiment of the disclosure.

In the drawings, the same reference numbers and any acronyms identify elements or acts with the same or similar structure or functionality for ease of understanding and convenience. To easily identify the discussion of any particular element or act, the most significant digit or digits in a reference number refer to the Figure number in which that element is first introduced.

DETAILED DESCRIPTION

Unless defined otherwise, technical and scientific terms used herein have the same meaning as commonly understood by one of ordinary skill in the art to which this invention belongs. Szycher's Dictionary of Medical Devices CRC Press, 1995, may provide useful guidance to many of the terms and phrases used herein. One skilled in the art will recognize many methods and materials similar or equivalent to those described herein, which could be used in the practice of the present invention. Indeed, the present invention is in no way limited to the methods and materials specifically described.

In some embodiments, properties such as dimensions, shapes, relative positions, and so forth, used to describe and claim certain embodiments of the invention are to be understood as being modified by the term "about."

As used herein, the term "subject" refers to a human or non-human animal (e.g., mouse, rat, ferret, dog, cat, cattle, swine, sheep, horse, or primate).

As used herein, the term "real-time" is defined to include a process occurring without intentional delay. For purposes of this disclosure, the term "real-time" will additionally be defined to include an action occurring within 10 seconds. For example, if fUS data is acquired, a real-time response (e.g., movement of a robotic limb) based on that data would occur within 10 seconds of the acquisition. Those skilled in the art will appreciate that most real-time processes will be performed in substantially less time than 10 seconds.

As used herein, the term "near real-time" is defined to include a process occurring without intentional delay, given the processing limitations of the system and the time required to acquire the data.

Various examples of the invention will now be described. The following description provides specific details for a thorough understanding and enabling description of these examples. One skilled in the relevant art will understand, however, that the invention may be practiced without many of these details. Likewise, one skilled in the relevant art will also understand that the invention can include many other obvious features not described in detail herein. Additionally, some well-known structures or functions may not be shown or described in detail below, so as to avoid unnecessarily obscuring the relevant description.

The terminology used below is to be interpreted in its broadest reasonable manner, even though it is being used in conjunction with a detailed description of certain specific examples of the invention. Indeed, certain terms may even be emphasized below; however, any terminology intended to be interpreted in any restricted manner will be overtly and specifically defined as such in this Detailed Description section.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations may be depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Overview

The present description relates to systems and methods for functional ultrasound imaging as neural interfaces. In particular, systems and methods are provided for decoding movement intentions using minimally invasive functional ultrasound imaging.

Figure 2:
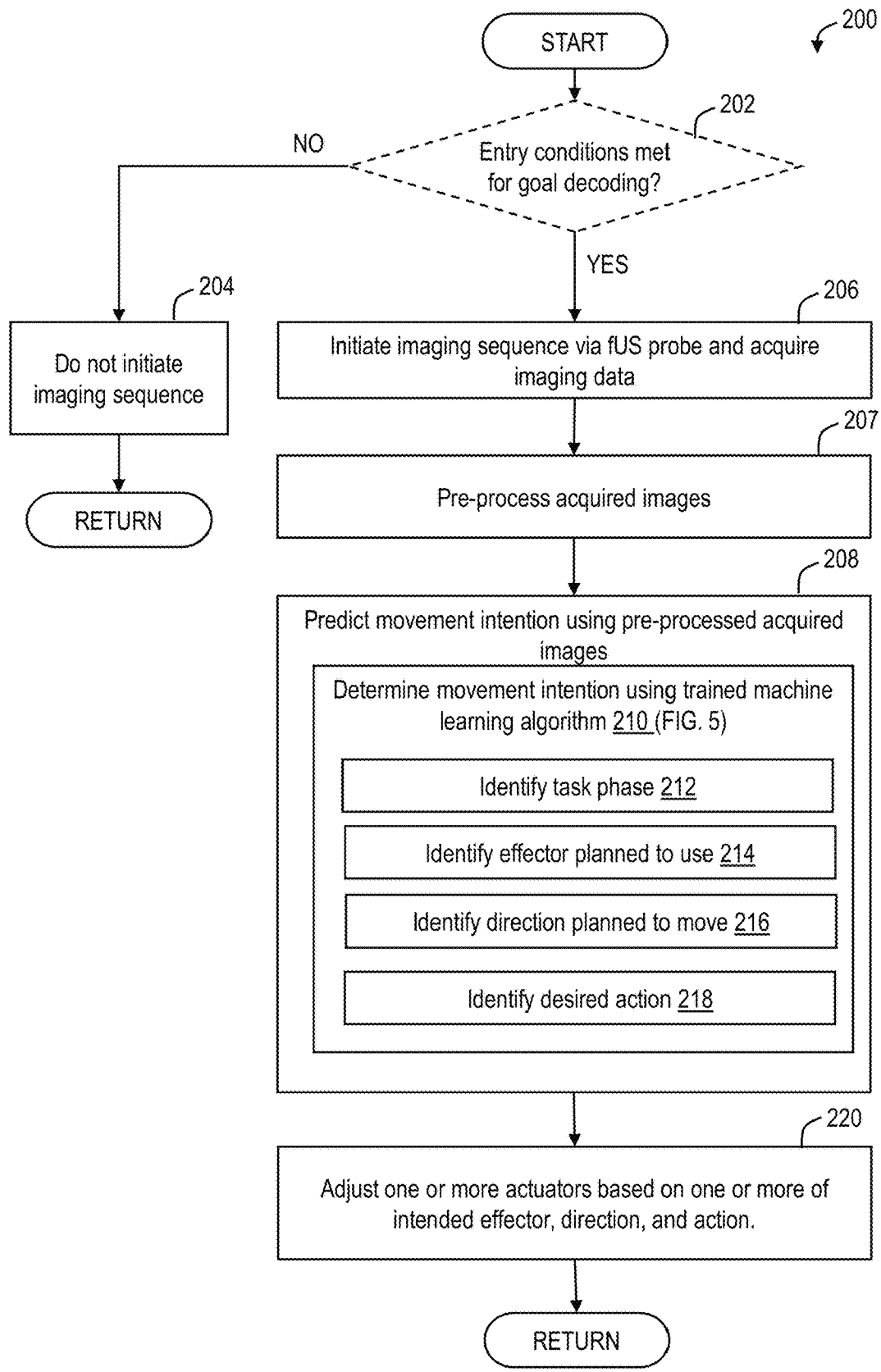
FIG. 2 is a flow chart illustrating an example method for predicting movement intentions in real-time using fUS, according to an embodiment of the disclosure.
Figure 3:
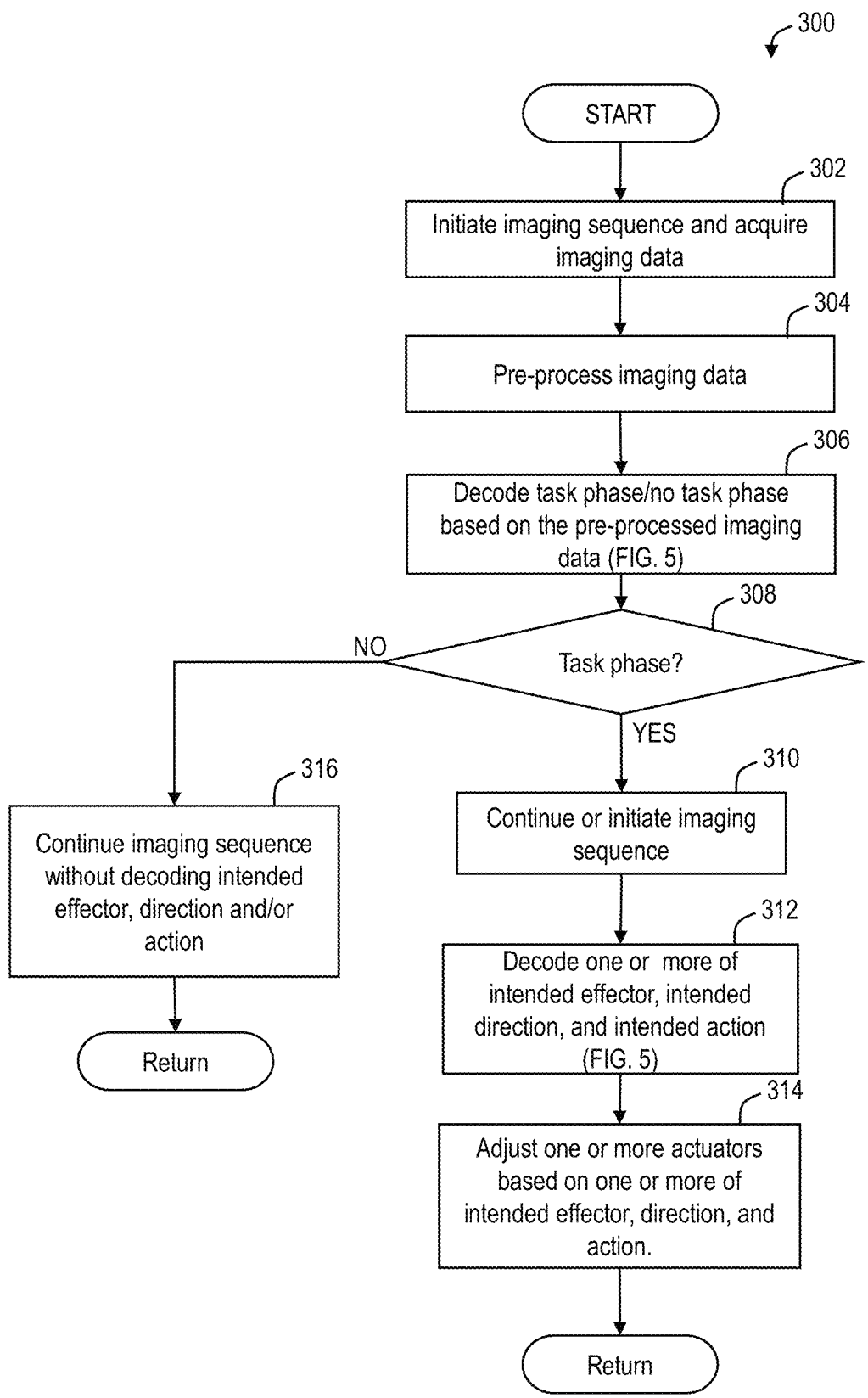
FIG. 3 is a flow chart illustrating an example method for predicting movement intentions in real-time using fUS, according to another embodiment of the disclosure.
Figure 5:
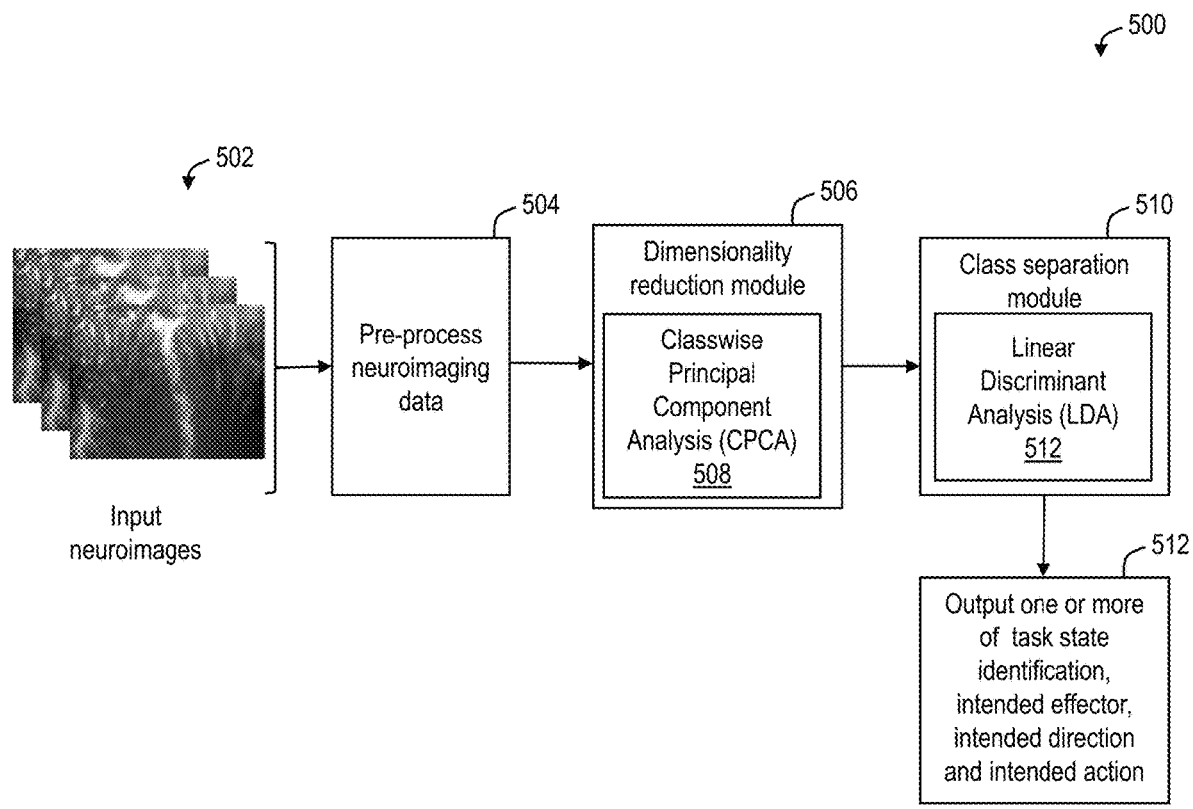
FIG. 5 is a block diagram illustrating an example decoding algorithm that is implemented to decode movement intentions using fUS imaging and on a single-trial basis, according to an embodiment of the disclosure.

Example neural interface systems that implement fUS for imaging neural activity in one or more areas of the brain are shown at FIGS. 1A and 1. Herein, fUS imaging is used to detect and decode one or more movement intentions that occur prior to onset of the actual movement by monitoring hemodynamic activity that correlates with neural activity in the brain. Example methods for acquiring fUS images and decoding movement intentions are illustrated at FIGS. 2 and 3. An example method for decoding sequential movements is shown at FIG. 5. Further, an embodiment of a decoding model architecture that is used for single-trial decoding of movement intentions using fUS images is shown at FIG. 5. Example anatomical regions of a NHP brain showing field of view of a fUS probe are shown at FIGS. 6A-6D. Experimental data showing various aspects of single trial decoding of movement intentions using fUS in NHPs are shown in FIGS. 7A-12B.

Technical advantages of the systems and methods for decoding movement intentions using fUS include reliable recording from large portions of the brain simultaneously with a single probe. fUS is also much less invasive than intracortical electrodes; it does not require penetration of the dura mater. This is a significant attribute, because it greatly reduces the risk level of the technique. Furthermore, while tissue reactions degrade the performance of chronic electrodes over time, fUS operates epidurally, precluding these reactions. In addition, the methods and systems described herein are highly adaptive due to wide field of view of fUS beams. This makes it much easier to target regions of interest. The wide field of view of fUS also enables decoding multiple parameters of intentions simultaneously. For example, wide field of view enables decoding of one or more of an intended effector to move, an intended direction, and/or an intended action simultaneously. Thus, by using fUS, multiple parameters of movement intentions may be decoded in real-time or near real-time, thereby improving speed of intention decoding as well as enabling correlating effector with direction, and/or action.

Further, fUS also provides access to cortical areas deep within sulci and subcortical brain structures that are difficult to target with electrophysiology. Finally, the mesoscopic view of neural populations made available by fUS is favorable for decoder generalization. Thus, the systems and methods described herein may be implemented for training and using decoders across days and/or subjects.

Further technical advantages include decoding movement intentions before corresponding movements are imagined, attempted, or executed using changes in cerebral blood flow. As a result, decoded intention signals can be delivered to a computing device, a robotic limb, or any assistive device in real-time or near real-time. This significantly reduces lag between intention to move and corresponding action executed by the device receiving the decoded intention signal. Example patient populations that may benefit from this technology include but not limited to, paralysis from stroke, Amyotropic Lateral Sclerosis (ALS), and spinal cord injuries.

Further, fUS BMI could also enable BMIs outside the motor system. Optimal applications might require access to deep brain structures or large fields of view on timescales compatible with hemodynamics. For example, cognitive BMIs such as state decoding of mood and other psychiatric states are of great interest due to the astounding prevalence of psychiatric disorders.

System

FIG. 1A illustrates a high-level block diagram of a neural interface system 100, according to an embodiment of the disclosure. The neural interface system 100 is configured to interface with the brain of a subject 106, perform, in real-time or near real-time, neuroimaging of the brain, and process, in real-time or near real-time, the neuroimaging data to determine one or more movement intentions of the subject 106. Further, the neural interface system 100 is configured to generate one or more control signals, in real time or near real-time, to a device 130 based on the one or more movement intentions determined from the neuroimaging data. The one or more movement intentions correspond to a cognitive state where a subject forms and develops motor planning activity before imagining, attempting, or executing a desired movement. As a non-limiting example, responsive to determining a movement intention of moving a desired effector (e.g., right arm) towards a desired direction (e.g., right), the neural interface system 100 may generate a control signal which may cause a corresponding prosthetic arm (e.g., right prosthetic arm) to move towards the desired direction (that is, right in this example) at the desired time. The desired effectors may be body effectors, including, but not limited to eyes, hands, arms, feet, legs, trunk, head, larynx, and tongue.

The neural interface system 100 comprises an ultrasound probe 102 for acquiring functional ultrasound (fUS) imaging of the brain, in real-time or near real-time. In particular, the ultrasound probe 102 may perform hemodynamic imaging of the brain to visualize changes in CBF using ultrafast Doppler angiography. fUS imaging enables a large field of view, and as such, a large area of the brain may be imaged using a single ultrasound probe. An example field of view of the ultrasound probe 102 may include various areas of posterior parietal cortex (PPC) of the brain including but not limited to lateral intraparietal (LIP) area, medial intraparietal (MIP) area, medial parietal area (MP), and ventral intraparietal (VIP) area.

In some embodiments, additionally or alternatively, fUS may be used to image hemodynamics in sensorimotor cortical areas and/or subcortical areas of the brain. For example, due to the large field of view of fUS systems, cortical areas deep within sulci and subcortical brain structures may be imaged in a minimally invasive manner that are otherwise inaccessible by electrodes.

Further, in some other embodiments, additionally or alternatively to PPC, fUS may be used to image hemodynamics in one or more of primary motor (M1), supplementary motor area (SMA), and premotor (PM) cortex of the brain.

In some examples, depending on a field of view of the ultrasound sound probe larger or smaller areas of the brain may be imaged. Accordingly, in some examples more than one probe may be utilized for imaging various areas of the brain. However, in some examples, a single probe may be sufficient for imaging desired areas of the brain. As such, a number of probes utilized may vary and may be based at least on a desired imaging area, size of skull, and field of view of the probes. In this way, by using fUS, neural activity can be visualized not only larger areas of brain but also in deeper areas of brain with improved spatial and temporal resolution and sensitivity.

In one example, the probe 102 may be positioned within a chamber 104 coupled to the subject's skull. For example, a cranial window may be surgically opened while maintaining a dura underneath the cranium intact. The probe 102 and the chamber 104 may be positioned over the cranial window to enable neuroimaging via the cranial window. In some examples, an acoustic coupling gel may be utilized to place the probe 102 in contact with the dura mater above the brain 105 within the chamber 104.

In another example, a neuroplastic cranial implant that replaces a portion of a subject's skull may be used. The neuroplastic cranial implant may comprise one or more miniaturized probes, for example. Implanted probes may also perform data processing and/or decoding in addition to transmitting data and/or power wirelessly through the scalp to a receiver.

In another example, a sonolucent material is used to replace a portion of a subject's skull (cranioplasty) above a brain region of interest. One or more ultrasound probes can afterward be positioned above the scalp, implant, and brain region of interest in a non-invasive way, for example, via a cranial cap comprising a stereotaxic frame supporting one or more ultrasound probes.

In yet another example, the one or more probes may be positioned above the subject's scalp and skull without craniotomy, for example, via a cranial cap comprising a stereotaxic frame supporting one or more ultrasound probes.

Further, the ultrasound probe 102 and its associated skull coupling portions (e.g., chamber 104, neuroplastic implants, stereotaxic frames, etc.) may be adapted for various skull shapes and sizes (e.g., adults, infants, etc.). Furthermore, the ultrasound probe 102 and the associated skull coupling portions may enable imaging of the brain while the subject is awake and/or moving.

Further, in one example, the probe 102 may be placed surface normal to the brain on top of the skull in order to acquire images from the posterior parietal cortex of the brain for movement decoding. However, in order to image a larger area of the brain or multiple brain areas, additional probes, each positioned at any desired angle with respect to the brain may be utilized.

The neural interface system 100 further includes an ultrasound scanning unit 110 (hereinafter "scanning unit 110" or "scanner 110") communicatively coupled to the ultrasound probe 102, and a real-time signal analysis and decoding system 120 communicatively coupled to the ultrasound scanning unit 110. Communication between the probe 102 and the scanning unit 110 may be wired, or wireless, or a combination thereof. Similarly, communication between the scanning unit 110 and the real-time signal analysis and decoding system 120 may be wired, or wireless, or a combination thereof. While the present example shows the scanning unit 110 and the real-time signal analysis and decoding system 120 separately, in some examples, the scanning unit 110 and the real-time signal analysis and decoding system 120 may be configured as a single unit. Thus, the ultrasound images acquired via the prone 102 may be processed by an integrated/embedded processor of the ultrasound scanner 110. In some examples, the real-time signal analysis and decoding system 120 and the scanning unit 110 may be separate but located within a common room. In some examples, the real-time signal analysis and decoding system 120 may be located in a remote location from the scanning unit 110. For example, the real-time signal analysis and decoding system may operate in a cloud-based server that has a distinct and remote location with respect to other components of the system 100, such as the probe 102 and scanning unit 110. Optionally, the scanning unit 110 and the real-time signal analysis and decoding system 120 may be a unitary system that is capable of being moved (e.g., portably) from room to room. For example, the unitary system may include wheels or be transported on a cart. Further, in some examples, the probe 102 may include an integrated scanning unit and/or an integrated real-time signal analysis and decoding system, and as such, fUS signal processing and decoding may be performed via the probe 102, and the decoded signals may be transmitted (e.g., wirelessly and/or wired) directly to the device 130.

In the illustrated embodiment, the neural interface system 100 includes a transmit beamformer 112 and transmitting unit 114 that drives an array of transducer elements (not shown) of the probe 102. The transducer elements may comprise piezoelectric crystals (or semiconductor based transducer elements) within probe 102 to emit pulsed ultrasonic signals into the brain 105 of the subject. In one example, the probe 102 may be a linear array probe, and may include a linear array of a number of transducer elements. The number of transducer elements may be 128, 256, or other number suitable for ultrasound imaging of the brain. Further, in some examples, the probe may be a phased array probe. Furthermore, any type of probe that may be configured to generate plane waves may be used.

Ultrasonic pulses emitted by the transducer elements are back-scattered from structures in the body, for example, blood vessels and surrounding tissue, to produce echoes that return to the transducer elements. In one example, a conventional ultrasound imaging with focused beam may be performed. The echoes are received by a receiving unit 116. The received echoes are provided to a receive beamformer 118 that performs beamforming and outputs an RF signal. The RF signal is then provided to the processor 111 that processes the RF signal. Alternatively, the processor 111 may include a complex demodulator (not shown) that demodulates the RF signal to form IQ data pairs representative of the echo signals. In some examples, the RF or IQ signal data may then be provided directly to a memory 114 for storage (for example, temporary storage).

In order to detect CBF changes in the brain, Doppler ultrasound imaging may be performed. Doppler ultrasound imaging detects movement of red blood cells by repeating ultrasonic pulses and evaluating temporal variations of successive backscattered signals. In one embodiment, ultrafast ultrasound imaging may be utilized based on plane wave emission for imaging CBF changes in brain tissue. Plane wave emission involves simultaneously exciting all transducer elements of the probe 102 to generate a plane wave. Accordingly, the ultrafast ultrasound imaging includes emitting a set of plane waves at titled angles in a desired range from a start degree to a final degree tilt of the probe 102 at a desired angular increment (e.g., 1 degree, 2 degrees, 3 degrees, etc.). An example desired range may be from −15 degrees to 15 degrees. In some examples, the desired range may be from approximately −30 degrees to +30 degrees. The above examples of ranges are for illustration, and any desired range may be implemented based on one or more of area, depth, and imaging system configurations. In some examples, an expected cerebral blood flow velocity may be considered in determining the desired range for imaging.

In one non-limiting example, the set of plane waves may be emitted at tilted angles of −6 to 6° at 3 degree increments. In another non-limiting example, the set of plane waves may be emitted at tilted angles from −7° to 8° at 1-degree increments.

Further, in some examples, a 3-dimensional (3D) fUS sequence may be utilized for imaging one or more desired areas of the brain. In one example, in order to acquire 3D fUS sequences, a 4-axis motorized stage including at least one translation along the x, y, and/or z axes, and one rotation about the z axis may be utilized. For example, a plurality of linear scans may be performed while moving the probe to successive planes to perform a fUS acquisition at each position to generate 3D imaging data. In another example, in order to acquire 3D fUS sequences, a 2D matrix array or row-column array probe may be utilized to acquire 3D imaging data in a synchronous manner, i.e. without moving the probe. 3D imaging data thus obtained may be processed for evaluating hemodynamic activity in the targeted areas of the brain and decoding movement intentions may be decoded. Thus, the systems and methods described herein for movement intention decoding using fUS may also be implemented by using 3D fUS imaging data without departing from the scope of the disclosure.

Imaging data from each angle is collected via the receiving unit 116. The backscattered signals from every point of the imaging plane are collected and provided to a receive beamformer 118 that performs a parallel beamforming procedure to output a corresponding RF signal. The RF signal may then be utilized by the processor 111 to generate corresponding ultrasonic image frames for each plane wave emission. Thus, a plurality of ultrasonic images may be obtained from the set of plane wave emissions. A total number of the plurality of ultrasonic images is based on acquisition time, a total number of angles, and pulse repetition frequency.

The plurality of ultrasonic images obtained from the set of plane wave emissions may then be added coherently to generate a high-contrast compound image. In one example, coherent compounding includes performing a virtual synthetic refocusing by combining the backscattered echoes of the set of plane wave emissions. Alternatively, the complex demodulator (not shown) may demodulate the RF signal to form IQ data representative of the echo signals. A set of IQ demodulated images may be obtained from the IQ data. The set of IQ demodulated may then be coherently summed to generate the high-contrast compound image. In some examples, the RF or IQ signal data may then be provided to the memory 113 for storage (for example, temporary storage).

Further, in order to image brain areas with desired spatial resolution, the probe 102 may be configured to transmit high-frequency ultrasonic emissions. For example, the ultrasound probe may have a central frequency of at least 5 MHz for fUS imaging for single-trial decoding. In particular, inventors have identified that functional hyperemia (that is, changes in cerebral blood flow corresponding to cognitive function) arises predominantly in microvasculature (sub-millimeter), and as such high-frequency ultrasonic emissions are utilized to improve spatial resolution to detect such signals. Further, as fUS enables brain tissue imaging at greater depths, movement intention decoding can be efficiently accomplished without invasive surgery that may be needed for an electrophysiology based BMI.

The processor 111 is configured to control operation of the neural interface system 100. For example, the processor 111 may include an image-processing module that receives image data (e.g., ultrasound signals in the form of RF signal data or IQ data pairs) and processes image data. For example, the image-processing module may process the ultrasound signals to generate volumes or frames of ultrasound information (e.g., ultrasound images) for displaying to the operator. In system 100, the image-processing module may be configured to perform one or more processing operations according to a plurality of selectable ultrasound modalities on the acquired ultrasound information. By way of example only, the ultrasound modalities may include color-flow, acoustic radiation force imaging (ARFI), B-mode, A-mode, M-mode, spectral Doppler, acoustic streaming, tissue Doppler module, C-scan, and elastography. The generated ultrasound images may be two-dimensional (2D) or three-dimensional (3D). When multiple two-dimensional (2D) images are obtained, the image-processing module may also be configured to stabilize or register the images.

Further, acquired ultrasound information may be processed in real-time or near real-time during an imaging session (or scanning session) as the echo signals are received. In some examples, an image memory may be included for storing processed slices of acquired ultrasound information that may be accessed at a later time. The image memory may comprise any known data storage medium, for example, a permanent storage medium, removable storage medium, and the like. Additionally, the image memory may be a non-transitory storage medium.

In operation, an ultrasound system may acquire data, for example, volumetric data sets by various techniques (for example, 3D scanning, real-time 3D imaging, volume scanning, 2D scanning with probes having positioning sensors, scanning using 2D or matrix array probes, and the like). In some examples, the ultrasound images of the neural interface system 100 may be generated, via the processor 111, from the acquired data, and displayed to an operator or user a display device of a user interface 119 communicatively coupled to the scanning unit 110.

In some examples, the processor 111 is operably connected to the user interface 119 that enables an operator to control at least some of the operations of the system 100. The user interface 119 may include hardware, firmware, software, or a combination thereof that enables a user (e.g., an operator) to directly or indirectly control operation of the system 100 and the various components thereof. The user interface 119 may include a display device (not shown) having a display area (not shown). In some embodiments, the user interface 119 may also include one or more input devices (not shown), such as a physical keyboard, mouse, and/or touchpad. In an exemplary embodiment, the display device 118 is a touch-sensitive display (e.g., touchscreen) that can detect a presence of a touch from the operator on the display area and can also identify a location of the touch in the display area. The display device also communicates information from the processor 111 to the operator by displaying the information to the operator. The display device may be configured to present information to the operator during one or more of an imaging session, and training session. The information presented may include ultrasound images, graphical elements, and user-selectable elements, for example.

The neural interface system 100 further includes the real-time signal analysis and decoding system 120 which may be utilized for decoding neural activity in real-time. In one example, neural activity may be determined based on hemodynamic changes, which can be visualized via fUS imaging. As discussed above, while the real-time signal analysis and decoding system 120 and the scanning unit 110 are shown separately, in some embodiments, the real-time signal analysis and decoding system 120 may be integrated within the scanning unit and/or the operations of the real-time signal analysis and decoding system 120 may be performed by the processor 111 and memory 113 of the scanning unit 110.

The real-time signal analysis and decoding system 120 is communicatively coupled to the ultrasound scanning unit 110, and receives ultrasound data from the scanning unit 110. In one example, the real-time signal analysis and decoding system 120 receives compounded ultrasound images, in real-time or near real-time, generated via the processor 111 based on plane wave emission via probe 102. The real-time signal analysis and decoding system 120 includes non-transitory memory 113 that stores a decoding module 126. The decoding module 126 may include a decoding model that is trained for decoding movement intentions of a subject by correlating neural activity in the brain using the compounded ultrasound images received from the scanning unit 110 with movement intention. The decoding model may be a machine learning model, and an example decoding model is shown and described with respect to FIG. 5. Accordingly, the decoding module 126 may include instructions for receiving imaging data acquired via an ultrasound probe, and implementing the decoding model for determining one or more movement intentions of a subject. In one example, the imaging data may include a plurality of CBF images generated by a performing power Doppler imaging sequence via an ultrasound probe 102. In one example, the CBF images are compound ultrasound images generated based on Doppler imaging of the brain.

Non-transitory memory 124 may further store a training module 127, which includes instructions for training the machine learning model stored in the decoding module 108. Training module 127 may include instructions that, when executed by processor 122, cause real-time signal analysis and decoding system 120 to train the decoding model using a training dataset. Example protocols implemented by the training module 110 may include learning techniques such as gradient descent algorithm, such that the decoding model can be trained and can classify input data that were not used for training.

Non-transitory memory 124 may also store an inference module (not depicted) that comprises instructions for testing new data with the trained decoding model. Further, non-transitory memory 124 may store image data 128 received from the ultrasound scanning unit 110. In some examples, the image data 128 may include a plurality of training datasets generated via the ultrasound scanning unit 110.

Real-time signal analysis and decoding system 120 may further include a user interface (not shown). The user interface may be a user input device, and may comprise one or more of a touchscreen, a keyboard, a mouse, a trackpad, a motion sensing camera, an eye tracking camera, and other device configured to enable a user to interact with and manipulate data within the processing system 120.

The real-time signal analysis and decoding system 120 may further include an actuation module 129 for generating one or more actuation signals in real-time based on one or more decoded movement intention (e.g., determined via the decoding model). In one example, the actuation module 129 may use a derived transformation rule to map an intended movement signal, s, into an action, a, for example, a target. Statistical decision theory may be used to derive the transformation rule. Factors in the derivations may include the set of possible intended movement signals, S, and the set of possible actions, A. The neuro-motor transform, d, is a mapping for S to A. Other factors in the derivation may include an intended target θ and a loss function which represents the error associated with taking an action, a, when the true intention was θ. These variables may be stored in a memory device, e.g., memory 124.

In some examples, two approaches may be used to derive the transformation rule: a probabilistic approach, involving the intermediate step of evaluating a probabilistic relation between s and θ and subsequent minimization of an expected loss to obtain a neuro-motor transformation (i.e., in those embodiments of the invention that relate to intended movement rather than, e.g., emotion); and a direct approach, involving direct construction of a neuro-motor transformation and minimizing the empirical loss evaluated over the training set. Once the actuation module maps an intended movement signal to an action, the actuation module 129 may generate an actuation signal indicative of the cognitive signal (that is, intended movement signal) and transmit the actuation signal to a device control system 131 of a device 130. The device control system 131 may use the actuation signal to adjust operation of one or more actuators 144, that may be configured to execute a movement based on the actuation signals generated by the actuation module 129. For example, adjusting the operation of one or more actuators 144 may include mimicking the subject's intended movement or perform another task (e.g., move a cursor, turn off the lights, perform home environmental temperature control adjustments) associated with the cognitive signal.

Thus, based on decoded intended movements, via the decoding module 126, one or more actuation signals may be transmitted to the device 130 communicatively coupled to the neural interface system 100. Further, the control system 131 is configured to receive signals from and send signals to the real-time signal analysis and decoding system 120 via a network. The network 230 may be wired, wireless, or various combinations of wired and wireless. In some examples, the actuation module 129 may be configured as a part of the device 130. Accordingly, in some examples, the device 130 may generate one or more actuation signals based on movement intention signals generated by an integrated decoding module. As a non-limiting example, based on a movement intention (e.g., move right hand to the right), the actuation module 129 may generate, in real-time, an actuation signal which is transmitted, in real-time, to the control system 131. The actuation signal may then be processed by the device control system 131 and transmitted to a corresponding actuator (e.g., a motor actuator of a right hand prosthetic limb) causing the actuator to execute the intended movement.

The device 130 may be, for example, a robotic prosthetic, a robotic orthotic, a computing device, a speech prosthetic or speller device, or a functional electrical stimulation device implanted into the subject's muscles for direct stimulation and control or any assistive device. In some examples, the device 130 may be a smart home device, and the actuation signal may be transmitted to the smart home controller to adjust operation of the smart home device (e.g., a smart home thermostat, a smart home light, etc.) without the need for using a prosthetic limb. Thus, the neural interface system 100 may interface with a control system of a device, without the use of a prosthetic limb. In some examples, the device may be a vehicle and the actuation signal may be transmitted to a vehicle controller to adjust operation of the vehicle (e.g., to lock/unlock door, to open/close door, etc.). Indeed, there are a wide range of tasks that can be controlled by a prosthetic that receives instruction based on the cognitive signals harnessed in various embodiments of the present disclosure. Reaches with a prosthetic limb could be readily accomplished. A cursor may be moved on a screen to control a computer device. Alternatively, the mental/emotional state of a subject (e.g., for paralyzed patients) may be assessed, as can intended value (e.g., thinking about a pencil to cause a computer program (e.g., Visio) to switch to a pencil tool, etc.). Other external devices that may be instructed with such signals, in accordance with alternate embodiments of the present invention, include, without limitation, a wheelchair or vehicle; a controller, such as a touch pad, keyboard, or combinations of the same; and a robotic hand. As is further described in the ensuing Experimental Results, the system can also decode additional concepts such as expected value. Still further applications for the system of the present invention can be readily identified and implemented by those of skill in the art.

In some examples, the neural interface system 100 may be communicatively coupled one or more devices. Accordingly, the neural interface system 100 may transmit control signals (based on decoded intention signals) simultaneously or sequentially to more than one device communicatively coupled to the neural interface system 100. For example, responsive to decoding movement intentions, the real-time signal analysis and decoding system 120 may generate and transmit a first control signal (e.g., based on decoding a first intended effector, such as arms, first direction, and/or first action) to a first device (e.g. robotic limb to grasp a cup) and simultaneously or sequentially, generate and transmit a second control signal (e.g., based on a second decoded intended effector such as eyes, second direction, and/or second action) to a second device (e.g., computer for cursor movement). Thus, in some examples, the neural interface system 100 may be configured to communicate with and/or adjust operation of more than one device.

In an embodiment, the actuation module 129 may use a feedback controller to monitor the response of the device, via one or more sensors 142, and compare it to, e.g., a predicted intended movement, and adjust actuation signals accordingly. For example, the feedback controller may include a training program to update a loss function variable used by the actuation module 129.

The subject may be required to perform multiple trials to build a database for the desired hemodynamic signals corresponding to a particular task. As the subject performs a trial, e.g., a reach task or brain control task, the neural data may be added to a database. The memory data may be decoded, e.g., using a trained decoding model, and used to control the prosthetic to perform a task corresponding to the cognitive signal. Other predictive models may alternatively be used to predict the intended movement or other cognitive instruction encoded by the neural signals.

Figure 1B:
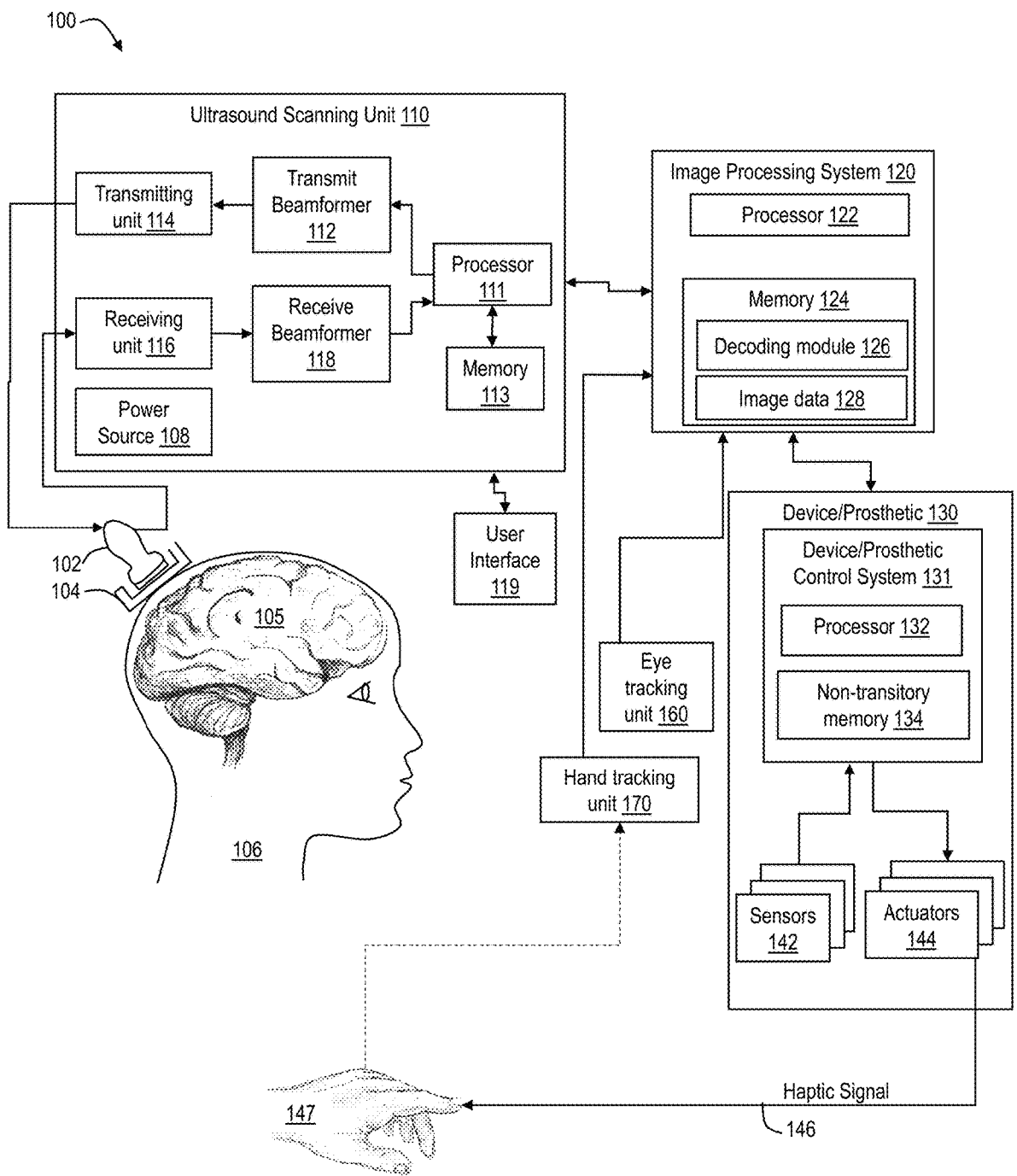
FIG. 1B is a block diagram of a neural interface system for real-time decoding of neural activity using functional ultrasound (fUS), according to an embodiment of the disclosure.

FIG. 1B shows another embodiment of the neural interface system 100, wherein an eye tracking unit 160 is communicatively coupled to the real-time signal analysis and decoding system 120. The eye tracker 160 may include one or more cameras, a processor, and memory. In one example, the eye tracker 160 may be utilized to identify whether to initiate image acquisition for decoding movement intention. For example, in general, vision precedes intended movement. As such, by monitoring eye movement and gaze, the neural interface system may receive information necessary to initiate ultrasound image acquisition. The eye tracker unit 160 may be a head-mounted unit, positioned within an environment of the subject (e.g., home), coupled to or integrated with a computing device (e.g., that may be operated by the subject) or any combination thereof. The eye tracker 160 may acquire gaze data and transmit gaze data to image processing unit 120. In one example, responsive to determining, via gaze data, that a subject is gazing at an object (e.g., a cup), the real-time signal analysis and decoding system 120 may send a signal to the scanning unit to initiate image acquisition.

In another example, additionally or alternatively, the eye tracking unit 160 may be utilized to determine whether a task has been completed. For example, determination of task completion, based on the gaze data, may be performed in addition to or alternative to other indications of task completion (e.g., signal from device 130 indicating that a desired actuation movement was completed, indication from a processor of a computing device that a cursor has moved to a desired position, etc.). Thus, the eye tracking unit 160 may be utilized to determine when to stop image acquisition, and/or if a next immediate task (or a next sequence in a task) is to be performed and therefore to continue imaging.

In further examples, the eye tracking unit 160 may be utilized during a training period when a new action is desired and thus a new movement intention is to be decoded (e.g., decoding a new intention that the decoding module has not been trained to classify). For example, a patient having the neural interface 100 for movement intention decoding may have a new smart home appliance installed in their home. The eye tracking unit 160 may be utilized to determine the gaze period with respect to the smart home appliance that may occur prior to task period. In some embodiments, the eye tracking unit 160 may facilitate the training period for the neural interface system 100 by providing labels for initiating acquire neural ultrasound images (e.g., task versus no task), decode movement intention (e.g., based on hemodynamic changes in the brain as the subject forms an intention to turn the switch ON), and/or completion of the movement intention.

In some embodiments, fUS imaging for decoding movement intentions may be periodically initiated (e.g., without assistance from the eye tracking unit 160). For example, during a waking period of the subject, the fUS imaging may be initiated periodically to decode movement intentions.

Further, a hand tracking unit 170 may be communicatively coupled to the real-time signal analysis and decoding system 120. In one example, the hand tracking unit 170 may be integrated with a robotic prosthetic and may include one or more sensors for determining a trajectory of the prosthetic arm. For example, the trajectory data may be utilized to determine when a task is completed or a status of a current task in order to coordinate fUS imaging and effector movement (e.g., hand movement).

In some examples, the hand tracking units 170 may also be utilized for training the decoding model. For example, the hand tracking unit 170 may be utilized to monitor movement of a test subject (e.g., a non-human primate) during training and validation of the decoding model.

In some examples, gaze data, and/or limb trajectory data may be processed by the real-time signal analysis and decoding system 120. In some other examples, gaze and/or limb trajectory data may be processed by respective integrated control systems.

In some examples, additionally or alternatively, one or more cameras (e.g., depth cameras) may be communicatively coupled to the real-time signal analysis and decoding system 100. The one or more cameras may be utilized to monitor subject position, gaze, limb position, etc., in addition to or alternative to gaze and/or hand tracking units.

Turning next to FIG. 2, it shows a flow chart illustrating a high-level method 200 for predicting movement intention of a subject. The method 200 may be executed by a processor, such as processor 122 or processor 111 or a combination thereof. The method 200 will be described below with respect to FIGS. 1A and 1B; however, it will be appreciated that the method 200 may be implemented by other similar systems without departing from the scope of the disclosure. The processor executing the method 200 includes a trained decoding model, such as model 500 at FIG. 5 below.

In one example, the method 200 may begin at 202. At 202, the method 200 includes determining whether entry conditions for goal decoding is met. That is, step 202 may be a decision point for determining whether to initiate fUS imaging, via a scanning unit and an ultrasound probe, for determining movement intention of a subject. This includes, in one example, monitoring a gaze of the subject and confirming whether the subject's gaze is fixated on an object (e.g., a cup) or a goal (e.g., cursor on a display portion of a computing device) for a threshold duration. The subject's gaze may be monitored in real-time via a gaze tracking unit, such as gaze tracking unit 160 at FIG. 1B. In one example, a real-time signal analysis and decoding system, such as system 120, may receive gaze data from the gaze tracking unit 160 and process gaze data in real-time. In another example, the gaze tracking unit 160 may process the gaze data in real-time and transmit a signal to the signal analysis and decoding system when entry conditions are met. Accordingly, in one example, the entry conditions at step 202 may be confirmed based on receiving an initiation signal from the gaze tracking unit.

In some examples, entry conditions may include confirming whether a training session is initiated. For example, a subject or a caregiver may initiate a training session, via a user interface of the neural interface system for example, to train the decoding module for a new task. In such cases, entry conditions are met when the training session is initiated.

If the answer at 202 is NO, the method 200 proceeds to 204. Responsive to entry conditions not being met, imaging sequence is not initiated. The method 200 then returns to 202 to continue monitoring for entry conditions.

If the answer at 202 is YES, the method 200 proceeds to 206. At 206, the method 200 includes performing fUS imaging sequence. In one example, performing fUS imaging includes performing plane wave imaging via an ultrasound probe, such as probe 102. Plane wave imaging is performed using plane wave imaging sequences at a desired pulse repetition frequency and desired ultrasonic frequency. The desired ultrasonic frequency is based on one or more of a desired spatial resolution and location of functional changes in CBF. In one example, the desired ultrasonic emission frequency is at least 15 MHz, which enables imaging of brain tissue with desired spatial resolution. A plane wave imaging sequence includes transmitting a plurality of plane waves with the probe tilted at various angles from an initial angulation to a final angulation at a desired incremental rate to generate a plurality of ultrasound images for each plane wave imaging sequence.

Next, at 207, the method 200 includes pre-processing the acquired images. Pre-processing the acquired images include generating a high-contrast compound image for each plane wave imaging sequence. A plurality of ultrasound images from a plane wave imaging sequence may be coherently compounded to generate a single ultrasound image (for each plane wave imaging sequence). In this way, a plurality of high contrast compounded ultrasound images are generated. Pre-processing the acquired images further includes performing applying a filtering process to the plurality of ultrasound images to separate tissue movement from red blood cell movement. In one example, a spatiotemporal clutter filtering based on single value decomposition may be employed. In another example, a high-pass filter may be utilized. Upon pre-processing the acquired images, the method 200 proceeds to 208.

Next, at 208, the method 200 includes predicting movement intention based on the pre-processed ultrasound images. For example, the inventors herein have identified that hemodynamic activity can be used to decode a timing and goal of an intended movement with high sensitivity. In particular, the inventors have identified that using fUS imaging to image hemodynamics, motor planning activity that precedes movement can be detected and decoded. Accordingly, the pre-processed ultrasound images (that is, filtered and compounded images) that show hemodynamic activity (that is, changes in CBF) are used to predict movement intention. For example, changes in Doppler signal provide indication of changes in CBF. Thus, Doppler signal change may be used to predict movement intention. Various parameters of the Doppler signal change, including timing of change, brain areas where the change is seen, and/or directionality of change may be used to predict movement intention. Further, movement intention prediction is performed using a trained machine learning decoding algorithm to identify one or more parameters of movement intention. Identification of one or more parameters of movement intention includes but not limited to identification of a task phase (step 212), identification of an effector planned to use (step 214), identification of direction planned to move (step 216), and identification of desired action (step 218). Details of the decoding algorithm (alternatively referred to as decoding model or simply decoder) will be described below at FIG. 5.

The above mentioned parameters of movement intention may be identified in real-time, or near real-time, and simultaneously using fUS image data. For example, the decoding algorithm may take the pre-processed compounded fUS images as input, and identify one or more of a task phase, an effector planned to use (e.g., hand, eye, leg, etc.), a direction planned to move (e.g., right, left, up, down, etc.), and an action planned to perform (reach, grasp, draw, release, tilt, etc.) before the movement is attempted or initiated.

Task phase includes a cognitive state wherein intentions for performing a desired movement are formed and developed prior to imagining the desired movement (that is, visualizing the desired movement), attempting to execute the desired movement, or executing the desired movement. The inventors have identified that by imaging hemodynamics (that is, changes in CBF) of the brain using fUS, the cognitive state when movement intentions are formed and developed can be detected and decoded. Thus, timing of movement intention can be detected and decoded. Accordingly, identification of the task phase based on Doppler signal change provides an indication of the timing when the subject intends to perform a movement. Further, during the task phase, various parameters of the movement intention, including one or more of the intended effector, intended direction, and intended action may be detected and decoded by imaging corresponding areas of the brain. Thus, in some examples, a first level decision may be based on the task phase, as described at FIG. 3 below.

The task phase may be identified based on Doppler signal changes over a duration in certain areas of the brain. Further, the areas of the brain that indicate task phase may be based on an effector (e.g., eye, hand, etc.) that the subject intends to move. As a non-limiting example, medial bank of intra parietal sulcus (ips) of a NHP may show a change in CBF when the NHP enters a task phase corresponding to performing a reach movement (corresponding to movement of an arm). Experimental data showing Doppler signal change in medial bank of ips indicating task phase correlating with reach movement intention is depicted in FIG. 8D. Thus, by evaluating and/or monitoring Doppler signal change in the medial bank of ips from the pre-processed ultrasound images, the machine learning algorithm may predict when the NHP has entered a task phase. Further, lateral intrapa-rietal area (LIP) of the brain is involved in planning saccade eye movements and shows changes in CBF when the NHP enters a task phase corresponding to performing an eye movement. Accordingly, Doppler signal change in the LIP area may also be monitored and/or evaluated to determine whether the NHP has entered a task phase. Experimental data showing Doppler signal change indicating task phase correlating with saccade movement intention in small vasculature outside of LIP is depicted in FIG. 7E. Similarly, one or more additional areas of the brain that show hemodynamic changes corresponding to intended movements may be monitored and/or evaluated by using the pre-processed ultrasound images to determine whether a subject has entered a task phase.

Similarly, the effector planned to use and the direction planned to move may be identified by monitoring hemodynamic activity (indicated by Doppler signal change) using fUS images in relevant areas of the brain. Due to wide field of view of fUS imaging, the various areas corresponding to effector and direction can be imaged simultaneously, which allows simultaneous decoding of the effector and direction, for example, which enables the use of fUS in decoding complex behaviors and in BMIs.

In one example, the plurality of ultrasound images may be processed in real-time, to determine one or more goals simultaneously. Information defining goals may include, for example, semantics (e.g. the concept of "light" could be used to turn on a lamp), location with respect to a multiple reference frames (e.g. the light is located to the right of the subject's hand, but to the left of their gaze), or specific visual cues (e.g. the light is of a distinct shape and/or color). Furthermore, the plurality of ultrasound images may be processed, in real-time, to determine the magnitude of one or more effectors simultaneously, for example, the intended velocity and magnitude of a movement or the degree of rotation of an effector. Thus, in addition to or alternative to movement intention decoding using the plurality of functional ultrasound images, one or more goals may be decoded simultaneously, wherein the goals include but not limited to performing a task without the use of a prosthetic limb, evaluating a target object's location with respect to multiple reference frames, and/or visual cues. Further, using the plurality of functional ultrasound images, magnitudes of movement intention may be decoded. The magnitudes of movement intentions include magnitudes of one or more effectors including but not limited to an intended velocity of an intended movement of an effector, an intended degree of rotation of the effector, and/or an intended distance of the intended movement.

Upon predicting one or more parameters of movement intention, the method 300 includes adjusting one or more actuators based on one or more of the intended effector, direction, and action. For example, an actuation signal may be generated corresponding to the predicted movement. In one example, the actuation signal may then be transmitted to an actuator controller of a prosthetic arm (e.g., motor controller of a right prosthetic arm) to adjust operation of an actuator (e.g., motor of the right prosthetic arm) to move the corresponding arm. In another example, the actuator may be a mouse actuator of a computing device, and the actuation signal may cause the mouse actuator to move a cursor in a desired direction.

Referring to FIG. 3, it shows a flow chart illustrating a high-level method 300 for decoding movement intentions according to task phase identification. The method 300 and all methods described herein may be executed by a processor, such as processor 122 or processor 111 or a combination thereof. The method 300 and all methods herein will be described below with respect to FIGS. 1A and 1B; however, it will be appreciated that the method 300 may be implemented by other similar systems without departing from the scope of the disclosure.

Step 302 including initiating imaging sequence and acquiring imaging data, and step 304 including pre-processing imaging data are similar to steps 206 and 207, and hence will not be repeated for the sake of brevity.

In this example, upon pre-processing imaging data, the method 300 proceeds to 306 at which the method 300 includes decoding task phase or no task phase based on the pre-processed images. The task phase or no-task phase is decoded using the trained decoding algorithm. Details of the decoding algorithm will be described below at FIG. 5. As discussed above, the task phase is determined based on Doppler signal changes indicated by pre-processed ultrasound images in task-related areas of the brain. No-task phase may be confirmed when Doppler signal changes from task-related areas of the brain do not reflect task activity, as determined by the decoder module 126. Experimental data showing decoding of task phase and no-task phase over a period of time in NHP is shown in FIG. 10C.

Task phase may be similar to memory phase in a trial of a NHP where the subject remembers the location of a target prior to executing a reach movement or a saccade movement to the target location. Examples of a saccade task, event-related average response maps, and waveforms depicting Doppler signal changes for a NHP subject during the saccade task is described below at FIGS. 7A-7I. Examples of a reach task, and corresponding event-related average response maps, and waveforms depicting Doppler signal changes for a NHP subject is described below at FIG. 8A-8G. While experimental data provided herein shows decoding of movement intentions in NHPs, it will be appreciated that the systems and methods described herein can be implemented for single trial decoding of movement intentions in any mammals, including humans.

Next, at 308, the method 300 includes determining whether a task phase is detected. If the answer is NO, the method 300 proceeds to 316. The method may continue imaging sequence without further decoding intended effector, direction, and/or action until task phase is confirmed. The method 300 then returns to step 302.

At 308, if the answer is YES, task phase is confirmed and the method 300 proceeds to 310. At 310, the method 300 includes continuing or initiating fUS imaging sequence.

Next, at 312, the method 300 may decode one or more of intended effector, direction and action as discussed above at steps 214, 216, and 218.

Upon identifying one or more the intended effector, direction and/or action, the method 300 includes, at 314, adjusting one or more actuators based on one or more of the intended effectors, direction and/or action.

In this way, fUS imaging enables decoding of the task phase that precedes movement. Further, by decoding timing of task phase and focusing decoding of the intended effector, intended direction, and/or intended action during the task phase, bandwidth of movement intention decoding using fUS is significantly increased.

Figure 4:
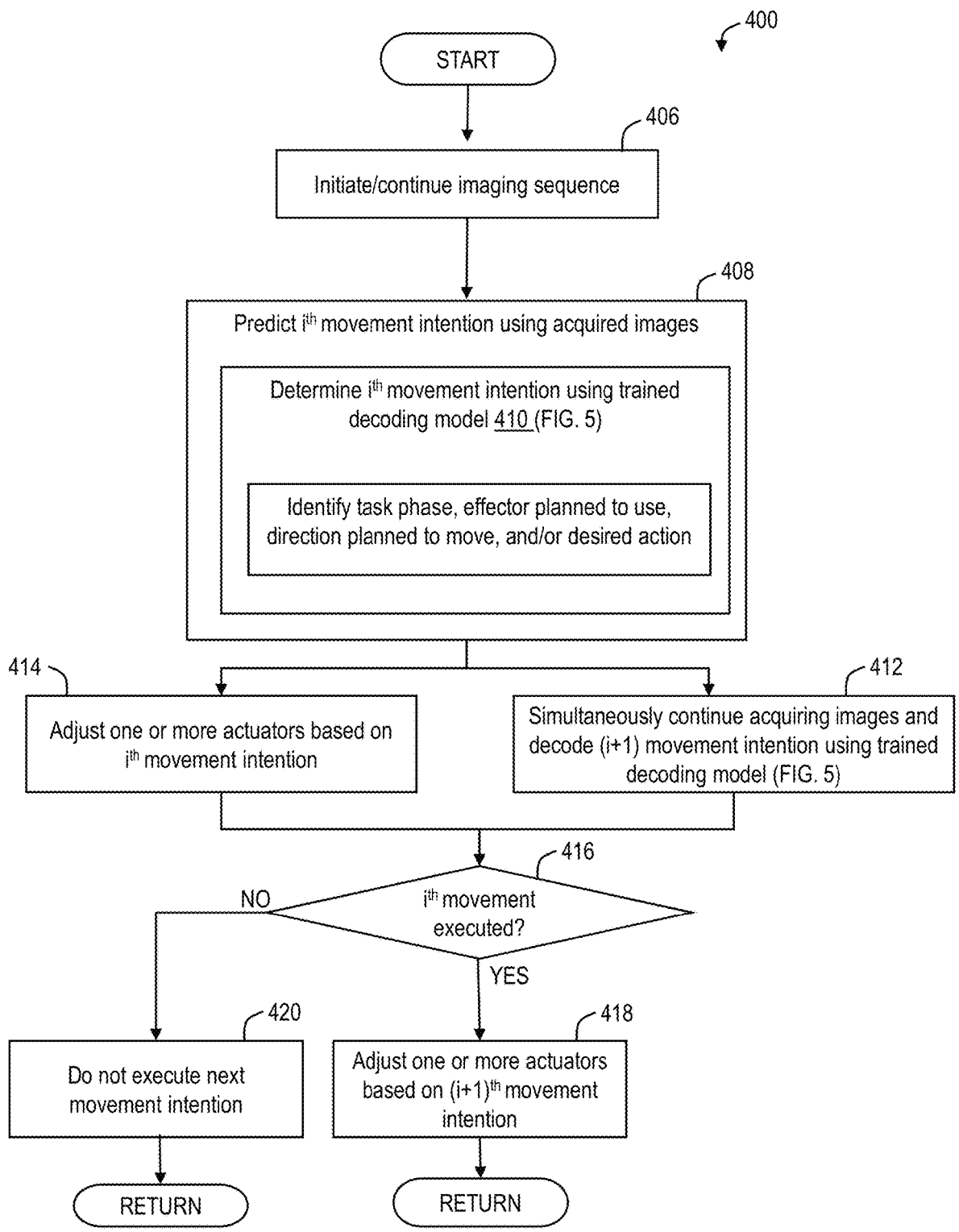
FIG. 4 is a flow chart illustrating an example method for predicting and executing sequential movement intentions, according to an embodiment of the disclosure.

FIG. 4 shows a flow chart illustrating a high-level method 400 for executing sequential movements based on decoding movement intentions using functional ultrasound images. The method 400 will be described using an example intended action of reaching toward a cup, picking up a cup, and bringing the cup toward the mouth to drink from the cup. It will be appreciated that the method 400 may be implemented for any intended action.

At 406, the method 400 includes initiating an ultrasound imaging sequence as discussed with respect to 206 at FIG. 2. Next, the method 400 includes predicting movement intention based on the acquired images. As discussed above, the acquired images may be pre-processed to differentiate tissue backscattering and tissue movement with respect to blood cell signals and blood cell movement prior to performing movement intention prediction. Further, a decoding algorithm, such as decoding model 500 described below, may use the pre-processed ultrasound images to identify one or more parameters of movement intention, including a task phase, effector planned to use, and direction planned to move. Further, the decoding algorithm may predict a desired action. In one example, a subject may first intend to reach toward a cup. Accordingly, first, the subject identifies the position of the cup in their vision. Once they've identified this goal, they imagine or attempt movement of the effector that they want to use (e.g. right arm) toward the cup. Meanwhile, the ultrasound probe is recording time series image data from the brain. The decoding algorithm decodes these data using the mapping/association from the training period to predict the subject's intended goal/direction (cup to the right) and effector (right arm).

Upon decoding the first intention, at 414, the method includes adjusting one or more actuators of one or more of a prosthetic arm and/or computing device based on the decoded movement intention. Continuing with the cup example, the processor sends an intended state of the actuator to the prosthetic limb. The limb begins to move to the desired goal without further intervention from the subject.

Simultaneously, at 412, the method 400 includes continuing image acquisition and decoding a next movement intention. In the cup example, while the prosthetic limb is moving towards the target (that is, cup), the subject, meanwhile, forms a new intention to grasp the cup. This sequential motor goal (that is grasp goal following the reach goal) is detected by the decoding algorithm.

Next, at 416, the method includes determining whether the previous movement has been executed. That is, the method 400 may determine whether the reach to the cup has been executed by the prosthetic limb. For example, one or more sensors of the prosthetic limb may send a signal to the processor indicating that the first intended movement of the prosthetic limb is complete. If previous movement execution is confirmed at 416, the method 400 proceeds to instruct the one or more actuators to execute the next decoded action. In the cup example, the method 400 proceeds to instruct the prosthetic limb to grip the cup. Thus, only after the prosthetic limb arrives at the cup, it receives the next command to grasp the cup. The prosthetic limb may detect the presence of the cup and execute the grasp.

Next, while the latest action is being executed (that is, while the limb is grasping the cup in this example) the subject forms a new intention to move the cup to their mouth, which is detected by the decoding algorithm (step 412) and the decoded intention is transmitted to the prosthetic limb. In this way, the sequence continues: intention 1, execution 1/intention2, execution 2/intention 3, . . . execution i/intention i+1.

Another non-limiting example may include moving a computer cursor to a target on a display or computer screen. First, the subject identifies the position of a goal on a display. Once they've identified this goal, they create the cognitive state associated with the cursor position defined during the training period. The processor, via the decoding algorithm, deciphers the intended goal and instructs the cursor to move to the intended target position.

FIG. 5 shows a block diagram illustrating a high-level architecture of an example machine learning decoding model 500 that is implemented by a processor, such as processor 111 or processor 122 for decoding movement intentions. During training phase, the decoding model 500 associates and models the relationship between the stimuli and cognitive state as represented by the brain activity recorded by ultrasound neuroimaging.

The decoding model 500 may receive ultrasound images acquired via an ultrasound probe and scanning unit of neural interface system, such as the probe 102 and scanning unit 110 of the neural interface system 100. Further, the acquired ultrasound images may be pre-processed, for example, filtered and registered. Pre-processing may include, when plane wave imaging sequence is used, generating compounded images from each plane wave imaging sequence. In some examples, all the image features may be used as input (that is, the whole image). In some other examples, a segmentation may be performed on the compounded images and selected regions of interest may be used as input. The pre-processed imaging data is then input into a dimensionality reduction module (block 506). Dimension reduction may be performed via classwise principal component analysis (CPCA) on the input features. Further, in one example, ordinary least square regression is applied on the CPCA transformed data to regress the CPCA transformed data to one or more of movement direction, and effector selection. Subsequently, linear discriminant analysis (LDA) is performed at the class separation module (block 508) to classify a movement direction plan and/or intended effector.

The inventors herein have identified that by applying CPCA and LDA on fUS imaging data, efficiency of the decoder is significantly improved.

In particular, class separability is improved by running linear discriminant analysis (LDA) on the CPCA-transformed data. Mathematically the transformed feature for each trial can be represented by:

$f = T_{LDA} \Phi_{CPCA}(d)$, where $d \in R^1$ are the flattened imaging data for a single trial, $\Phi_{CPCA}$ is the piecewise linear CPCA transformation, and $T_{LDA}$ is the LDA transformation. $\Phi_{CPCA}$ is physically related to space and time and thus can be viewed within the context of physiological meaning.

Subsequently, Bayes rule is used to calculate the posterior probabilities of each class given the observed feature space.

In one example, for movement direction classification, because CPCA is a piecewise function, posterior probabilities are calculated twice, once for each class, resulting in four posterior likelihoods: $P_L(L|f^*)$; $P_L(R|f^*)$; $P_R(L|f^*)$; $P_R(R|f^*)$, where $f^*$ represents the observation, $P_L$ and $P_R$ represent the posterior probabilities in the CPCA subspaces created with training data from left-directed and right-directed trials, respectively. Finally, the optimal principal component vectors and corresponding discriminant hyperplane from the subspace with the highest posterior probability. These findings are then used to predict the behavioral variable of interest for each trial in the testing set. That is $f^*$ from fUS imaging data is computed for each trial in the testing set to predict the upcoming movement direction.

The decoding model 500 is trained using imaging datasets obtained during trials. A trial may include a plurality of phases that are executed in a sequence over time by a subject. Multiple trials may be included in a session during a training phase. Using the decoding model 500 based on CPCA and LDA, a number of trials required to train the decoding algorithm to decode movement intentions from fUS imaging data for a specific task is greatly reduced. Specifically, single-trial decoding of movement intentions is enabled by combining fUS with the decoding model based on CPCA and LDA. Experimental data illustrating single trial decoding is shown at FIGS. 9A-9D.

In one example, a trial may include a fixation phase when a subject's gaze is fixated at a target. The target may be an object (e.g., cup), an image on a screen (e.g., cursor) or any object with respect to which a movement may be performed. The fixation phase may correspond to a gaze period of a cognitive state of a subject, which precedes movement intention and subsequent movement. The trial may further include a memory phase during which a movement intention is formed before attempting or executing a movement. In one example, during the memory phase of a trial, a subject may be asked to form an intention to perform a specified movement with respect to the target but not attempt to execute or execute the specified movement. The specified movement may involve one or more specific effectors (e.g., a hand, or eyes) and a specified direction (e.g., right, left, up, down, etc.). In some examples, the specified movement may involve a desired action (e.g., grab, release, pull, push, etc.). Further, in some examples, a cue may be provided with respect to a target to aid in the memory phase. The trial may conclude with a movement phase where the subject executes the specified movement.

During the training, a plurality of fUS images are acquired across trials, beamformed to functional images, and pre-processed. In the case of offline validation, the plurality of fUS images are then separated into training datasets and test datasets. The training dataset is labelled according to actual movement direction and effector. The decoding model is then trained with the training dataset. An example data flow for movement intention decoding comprises aligning fUS image time series with behavioral labels, performing feature selection, dimensionality reduction and class discrimination, and finally, performing performance evaluation including cross-validation in the case of offline analysis. An example single trial decoding of intended movement direction is described with respect to FIGS. 9A-9D below.

The trained decoding model 500 may classify memory phase (also referred to herein as task phase). Thus, using fUS imaging and the trained decoding model, movement intention prior to the actual movement execution or initiation of the actual movement may be detected. Further, the trained decoding model may classify an effector (e.g., eye versus hand) that the subject intends to use as well as a direction that the subject intends to move (e.g., right versus left).

Further still, the decoding model 500 may be trained to classify an action (e.g., grab versus release). While the above examples illustrate binary classification outputs, the decoding model may be trained to perform many classifications in parallel or to regress continuous variables (e.g., hand position coordinates).

Further, the decoding model 500 may simultaneously classify effector and direction. Thus, the decoding model 500 may perform simultaneous effector and direction decoding.

The above example shows the decoding model modelling the relationship between the stimuli and cognitive state using CPCA and LDA. It will be appreciated that this relationship can be defined by decoding or machine learning methods including, but not limited to, linear regression such as ordinary least squares regression, principal component analysis, classwise principal component analysis, information discriminant analysis, or linear discriminant analysis or any combination thereof. Furthermore, relationships between many stimuli or complex stimuli and cognitive state can be defined using artificial neural networks including, but not limited to convolutional neural networks, multilayer perceptron networks, and transformer neural networks, trained by optimization algorithms including, but not limited to, gradient descent, stochastic gradient descent, adagrad, and/or adam.

The technical advantages of the neural interface systems and methods include simultaneous effector and direction decoding. In addition to direction and effector, a task versus no-task phase is decoded. This is a critical step in closed-loop feedback environments such as BMI, where the user gates their own movement or the decoder is otherwise not privy to movement or task timing information. Furthermore, simultaneous decoding of task state, direction, and effector enables the use of fUS in decoding complex behaviors as well as improving BMI performance.

In one embodiment, a neural interface system comprises at least one ultrasound probe; a controller storing instructions in non-transitory memory that when executed cause the controller to: acquire, via the at least one ultrasound transducer, a plurality of functional ultrasound images; process the plurality of functional ultrasound images, in real-time or near real-time, to determine one or more movement intentions; and adjust one or more actuators of a device, in real-time or near real-time, according to the one or more movement intentions, the device communicatively coupled to the controller; wherein the at least one ultrasound transducer is positioned to image an area of a brain of a subject and wherein the one or more movement intentions includes an intended body effector and/or an intended direction to move the intended body effector. In one example of the neural interface system, process the plurality of functional ultrasound images, in real-time or near real-time, to determine one or more movement intentions comprises determining Doppler signal changes in the area of the brain.

In another embodiment, a neural interface system comprises one or more ultrasound transducers positioned to image an area of a brain of a subject; an ultrasound scanning unit comprising one or more processors, the one or more processors storing instructions in non-transitory memory that when executed cause the one or more processors to: acquire, via the one or more ultrasound transducers, a plurality of ultrasound images; process the plurality of ultrasound images, in real-time, to determine one or more movement intention parameters, wherein the one or more movement intention parameters include a timing indication of movement intention. In one example of the neural interface system, the one or more movement intention parameters include one or more intended movement effectors and one or more corresponding intended movement directions. In another example of the neural interface system, process the plurality of ultrasound images, in real-time, to determine one or more movement intention parameters comprises responsive to confirming a task phase based on the timing indication of movement intention, determining one or more of an intended movement effector and an intended movement direction of the intended movement effector.

EXAMPLES

The following examples are provided to better illustrate the claimed invention and are not intended to be interpreted as limiting the scope of the invention. To the extent that specific materials or steps are mentioned, it is merely for purposes of illustration and is not intended to limit the invention. One skilled in the art may develop equivalent trials, means or reactants without the exercise of inventive capacity and without departing from the scope of the invention.

FIGS. 6A-6F show example anatomical scanning regions in NHP. In particular, FIGS. 6A and 6B show illustrations of craniotomy field of view 602 in the axial plane and coronal cross-section respectively, overlaid on a NHP brain atlas. The 24×24-mm (inner dimension) chambers were placed surface normal to the brain on top of the craniotomized skull.

FIGS. 6C and 6D show 3D vascular maps for monkey L and monkey H. The field of view included the central and intraparietal sulci for both monkeys. FIGS. 6E and 6F illustrate representative slices for monkey L and monkey H showing the intraparietal sulcus (dotted line, labeled ips) with orientation markers (1, lateral or left; r, right; m, medial; v, ventral; d, dorsal; a, anterior; p, posterior).

To look for goal-related hemodynamic signals in the PPC, fUS images from NHPs were acquired using a miniaturized 15-MHz, linear array transducer placed on the dura via a cranial window. The transducer provided a spatial resolution of 100 µm×100 µm in-plane, slice thicknesses of ~400 µm, covering a plane with a width of 12.8 mm and penetration depth of 16 mm. As shown in FIGS. 6A and 6B, the probe was positioned surface-normal in a coronal orientation above the PPC. Planes of interest for each animal from the volumes available (FIGS. 6C-6F) were then selected. Specifically, planes that captured both the lateral and medial banks of the intraparietal sulcus (ips) within a single image and exhibited behaviorally tuned hemodynamic activity were chosen. Further, a plane-wave imaging sequence at a pulse repetition frequency of 7,500 Hz was used and the frames collected from a 500-ms period each second were compounded to form power Doppler images with a 1 Hz refresh rate.

While the above example shows imaging planes for ips, as discussed above at FIG. 1A, imaging area and/or depth may be increased. Further, multiple areas may be imaged to acquire imaging data for decoding intention. Further, in some examples, ultrasonic emission frequency may be greater than 15 MHz to further increase spatial resolution. Conversely, for example, in order to image deeper areas of the brain, such as subcortical areas, ultrasonic emission frequency may be decreased below 15 MHz to improve imaging depth and field of view.

Hemodynamic Response During Memory-Guided Saccades

Figure 7A:
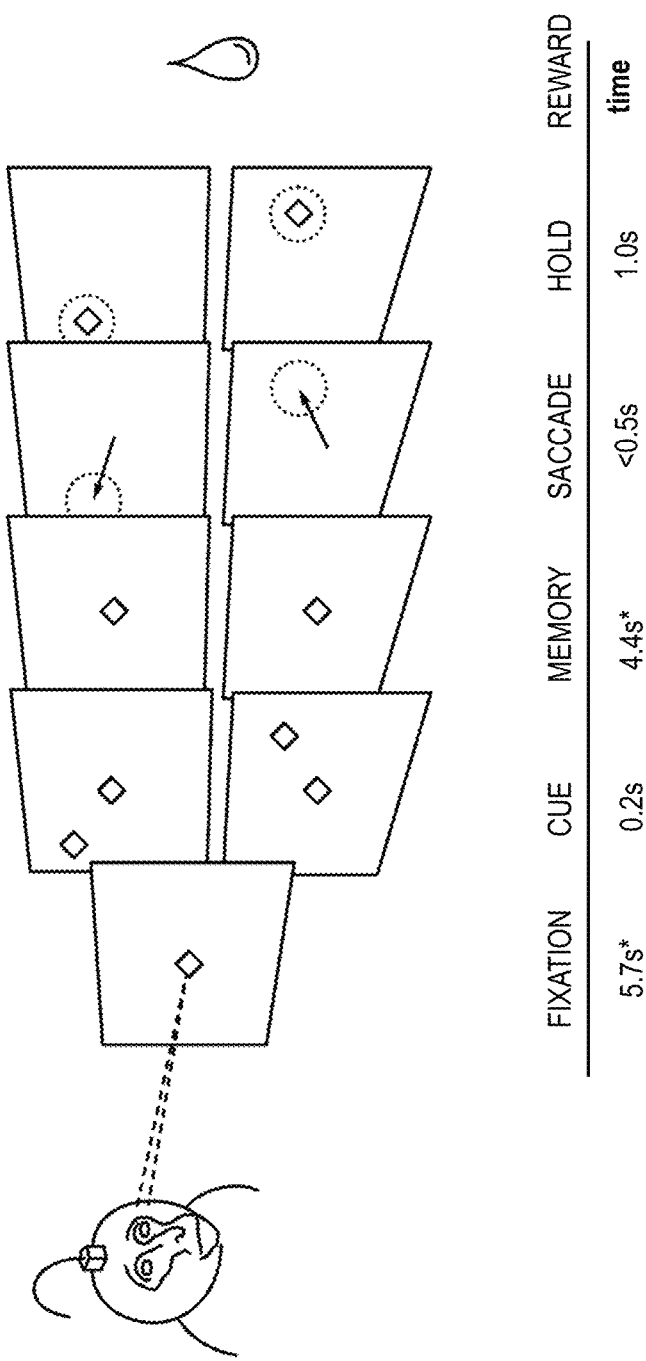

Next, FIGS. 7A-7I show an example saccade task, and event related response maps and waveforms during the saccade tasks performed by monkey L and monkey H. In particular, FIG. 7A shows an example saccade trial. The trial started with the animals fixating on a central cue (red diamond). Next, a target cue (red diamond) was flashed on either the left or right visual field. During a memory period, the animals had to remember its location while continuing to fixate on the center cue. When the center was extinguished (go signal), the animals performed a saccade to the remembered peripheral target location and maintained eye fixation before receiving a reward. *Mean values across sessions shown; the fixation and memory periods were consistent within each session but varied across sessions from 5.4 to 6.3 s and 4.0 to 5.1 s, respectively, depending on the animals' level of training. The fixation and memory periods were subject to 400 ms of jitter to preclude the animal from anticipating the change(s) of the trial phase. FIGS. 7B-7F show Representative activity map and event-related average (ERA) waveforms of CBV change within labeled regions of interest during memory-guided saccades for monkey L.

FIG. 7B is a statistical map showing localized areas with significantly higher signal change (SC) (one-sided t test of area under the curve, p<0.01) during the memory delay phase for right-cued compared to left-cued saccades, i.e., vascular patches of contralaterally tuned activity. FIGS. 7C and 7D show ERA waveforms in LIP displaying lateralized tuning specific to local populations. FIG. 7E shows small vasculature outside of LIP exhibiting event-related structure that is tuned to task structure but not target direction. FIG. 7F shows vessels that perfuse large areas of cortex indicating that these areas do not exhibit event-related signal.

FIGS. 7G-7I show activity map and ERA waveforms within labeled regions of interest for monkey H. In particular, FIG. 7G shows map for monkey H and ERA waveforms showing lateralized tuning in LIP are depicted in FIG. 7H. Further, FIG. 7I shows that target tuning also appears in medial parietal area (MP) for monkey H. FIGS. 7C-7F share a common range (9% SC), as do FIGS. 7H and 7I (14%). ERAs are displayed as means across trials, and thinner lines on either side of thicker lines represent standard error (SEM).

To resolve goal-specific hemodynamic changes within single trials, two NHPs were trained to perform memory-delayed instructed saccades. Specifically, the monkeys were required to memorize the location of a cue presented in either the left or right hemifield and execute the movement once the center fixation cue extinguished (FIG. 7A). The memory phase was chosen to be sufficiently long (from 4.0 to 5.1 s depending on the animals' training and success rate, with a mean of 4.4 s across sessions) to capture hemodynamic changes. fUS data was collected while each animal (N=2) performed memory-delayed saccades. A total of 2,441 trials over 16 days (1,209 from monkey H and 1,232 from monkey L) were collected.

Statistical parametric maps based on the Student's t test (one sided with false discovery rate [FDR] correction) were used to visualize patterns of lateralized activity in PPC (FIGS. 7B and 7G). Event-related average (ERA) changes of cerebral blood volume (CBV) were observed throughout the task from localized regions (FIGS. 7C-7F, 7H, and 7I). Spatial response fields of laterally tuned hemodynamic activity appeared on the lateral bank of ips (i.e., in LIP). Specifically, ERAs from LIP show higher memory phase responses to contralateral (right) compared to ipsilateral (left)-cued trials (one-sided t test of area under the curve during memory phase, t test p<0.001).

Monkey H exhibited a similar direction-tuned response in the presumed medial parietal area (MP), a small patch of cortex on the medial wall of the hemisphere (this area effect was not recorded in monkey L, because MP was outside the imaging plane). This tuning supports previous evidence of MP's role in directional eye movement. In contrast, focal regions of microvasculature outside the LIP also showed strong event-related responses to the task onset but were not tuned to target direction (e.g., FIG. 7E).

Memory-Delayed Reaches

Figure 8A:
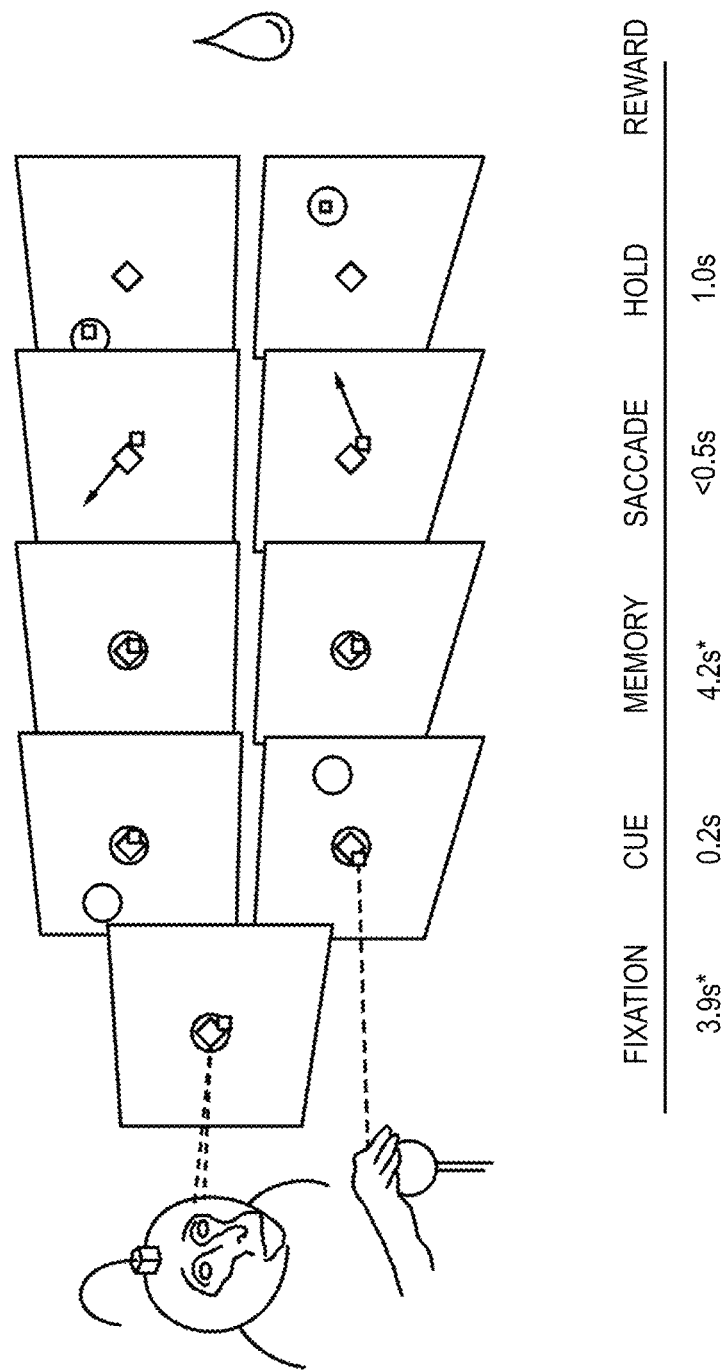

FIGS. 8A-8G show example reach task, event related response map, and waveforms. FIG. 8A shows a memory-guided reaching task using a 2D joystick. A trial started with the animal fixating on a central cue (red diamond) and positioning the joystick to its center (green circle). Next, a target (green circle) was flashed on either the left or right visual field. The animal memorized its location while fixating eye and hand on the center cue. When the hand center cue was extinguished (go signal), the animal performed a reach to the remembered target location and maintained the position before receiving a reward. Importantly, eye fixation was maintained throughout the entire trial. *Mean values across sessions shown; the fixation and memory periods were consistent within each session but varied across sessions from 2.5 to 5.9 s and 3.2 to 5.2 s, respectively. The fixation and memory periods were subject to 400 ms of jitter to preclude the animal from anticipating the change(s) of the trial phase. FIG. 8B is a statistical map showing localized areas with significantly higher SC (one-sided t test of area under the curve, p<0.01, false discovery rate [FDR] corrected for number of pixels in image) during the memory delay phase for right-cued compared to left-cued reaches (i.e., vascular patches of contralaterally tuned activity). FIG. 8C shows ERA waveforms from the lateral bank of ips revealing lateralized tuning in reaching movements. FIG. 8D shows ERA waveforms in the medial bank of ips exhibiting a population with bilateral tuning to reaching movements. ERAs are displayed as means across trials, and thinner lines represent standard error (SEM). FIGS. 8E-8G show statistical map and ERA waveforms from monkey H.

In a second experiment, fUS signals were collected while each NHP performed memory reaches. In total, 1,480 trials (543 from monkey H and 937 from monkey L) over 8 sessions were collected. The task was similar to that of saccades, but the animal's gaze remained fixated throughout the trial, including during the fixation, memory, and reach movement phases (FIG. 8A). The memory phase ranged from 3.2 to 5.2 s depending on the animals' training and success rate (mean, 4.2 s across sessions). ERAs on the lateral bank of ips reveal populations with direction-specific tuning (FIGS. 8C, 8D, 8F, and 8G). MP, which was responsive to saccade planning for monkey H (FIG. 7I), was not responsive to reach planning. Populations on the medial bank in the putative PRR do not exhibit lateralized tuning but do show bilateral tuning to the movement (FIGS. 8D and 8G). These results are consistent with electrophysiological recordings, in which the PRR neurons as a population encode both hemispaces, whereas LIP neurons largely encode the contralateral space.

The above experimental data in FIGS. 7A-7I and in FIGS. 8A-8G illustrate that hemodynamic changes occur that correspond to movement intentions and as such, Doppler signal changes can be used to decode movement intention signals, which may then be used for controlling movement via one or more assistive devices (e.g., robotic prosthesis, computing device, etc.)

Single-Trial Decoding

FIGS. 9A-9D illustrate example single-trial decoding of intended movement direction. Training images were separated from testing data according to the cross-validation technique being used. Movement intention predictions were made for single trials based on the dimensionality reduction and a classification model built by the training data with corresponding class labels (i.e., actual movement direction). FIG. 9A shows decoding accuracy as a function of time across all datasets. FIG. 9B shows decoding accuracy as a function of the number of trials used to train the decoder. Data points in FIGS. 9A and 9B are means, and thinner lines represent standard error (SEM) across sessions. FIG. 9C shows cross-temporal decoder accuracy, using all combinations of training and testing data with a 1-s sliding window. Results are shown in an example session for each animal. Significance threshold is shown as a contour line (p<0.05, FDR corrected). Training the classifiers during the memory or movement phase enabled successful decoding of the memory and movement phases. FIG. 9D shows representative decoder weighting maps (monkey L). The top 10% most heavily weighted voxels are shown as a function of space and time before the go cue was given, overlaid on the vascular map.

The direction of upcoming movements was determined using single trials of fUS data. Briefly, classwise principal component analysis (CPCA) was used to reduce data dimensionality. Then, ordinary least-squares regression (OLSR) was used to regress the transformed fUS data (from the memory delay period) to the movement direction (i.e., class label). Finally, linear discriminant analysis (LDA) was used to classify the resulting value for each trial as a presumed left or right movement plan. All reported results were generated using a 10-fold cross-validation. Saccade direction prediction accuracy within a session (i.e., decoded from the memory delay) ranged from 61.5% (binomial test versus chance level, p=0.012) to 100% ($p<0.001$) on a given 30-min run. The mean accuracy across all sessions and runs was 78.6% ($p<0.001$). Reach direction prediction accuracy ranged from 73.0% (binomial test versus chance level, $p<0.001$) to 100% ($p<0.001$). The mean accuracy across all sessions and runs was 88.5% ($p<0.001$).

To analyze the temporal evolution of direction-specific information in PPC, we attempted to decode the movement direction across time through the trial phases (fixation, memory, and movement). For each time point, we accumulated the preceding data. For example, at t=2 s, we included imaging data from t=0-2 s (where t=0 s corresponds to the beginning of fixation). The resulting cross-validated accuracy curves (FIG. 9A) show accuracy at chance level during the fixation phase, increasing discriminability during the memory phase, and sustained decode accuracy during the movement phase. During the memory phase, decoder accuracy improved, surpassing significance 2.08 s+0.82 s after the monkey received the target cue for saccades (2.32 s+0.82 s before moving, binomial test versus chance level, $p<0.05$, Bonferroni corrected for 18 comparisons across time) and 1.92 s+1.4 s or reaches (2.28 s+1.4 s before moving). Decoding accuracy be-tween saccades and reaches was not significantly different.

To determine the amount of data required to achieve maximum decoder accuracy, trials were systematically removed from the training set (FIG. 9C). Using just 27 trials, decoder accuracy reached significance for all datasets (binomial test, $p<0.05$) and continued to increase. Decoder accuracy reached a maximum when given 75 trials of training data, on average.

In order to determine whether the decoder is decoding the neural correlates of positions, trajectories, or goals, a cross-temporal decoding technique was used. Therein, a is sliding window of data was used to train the decoder and then attempted to decode the intended direction from another 1-s sliding window. This process for all time points through the trial duration, resulting in an n×n array of accuracies, where n is the number of time windows tested. Cross-validated accuracy was significantly above chance level throughout the memory and movement phases (FIG. 9C, dashed line, binomial test versus chance level, $p<0.05$, Bonferroni corrected for 18 time points).

In other words, the information decoded from this brain region was highly similar during movement preparation and execution. This result suggests that this area is encoding movement plans, visuo-spatial attention, or both. Distinct spatial locations within PPC encoded this information, a fact reflected in the variable weighting assigned to each voxel in the decoding algorithm. The decoder placed the highest weightings in area LIP (FIG. 9D). This also agrees with the canonical function of this region.

Decoding Memory Period, Effector, and Direction

Figure 10A:
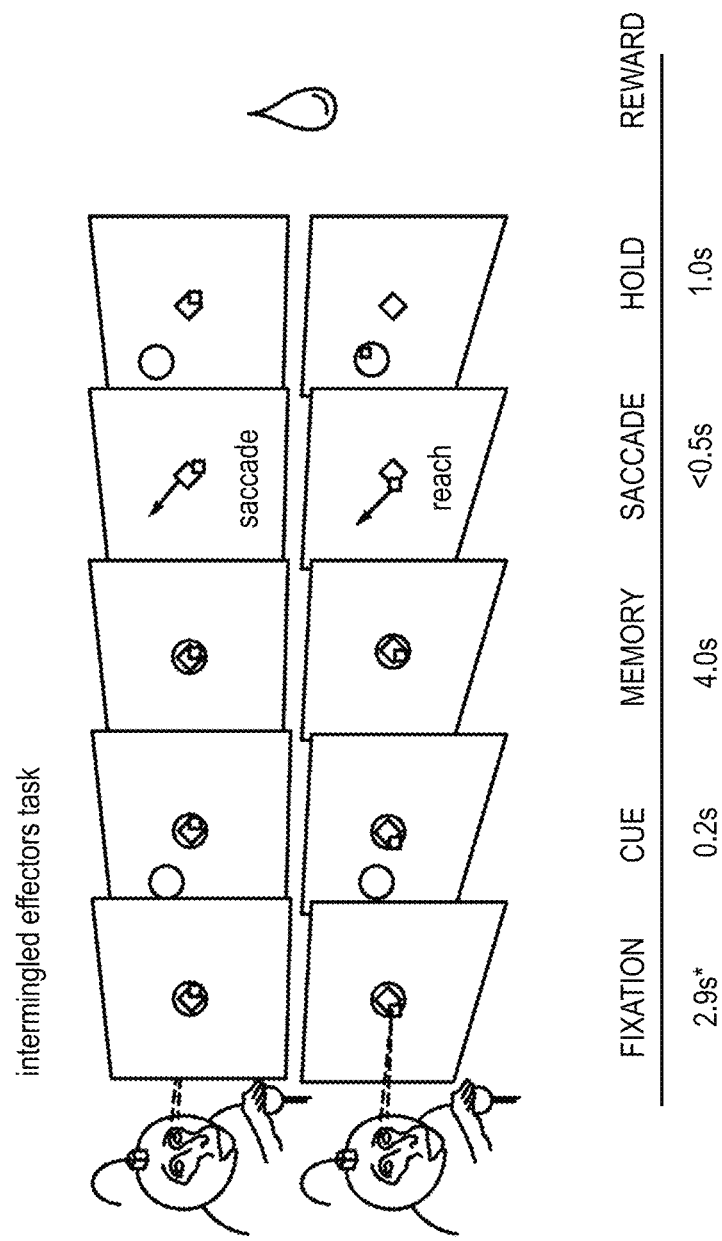
FIGS. 10A-10C depict example decoding task, effector, and direction simultaneously, according to an embodiment of the disclosure.
Figure 10B:
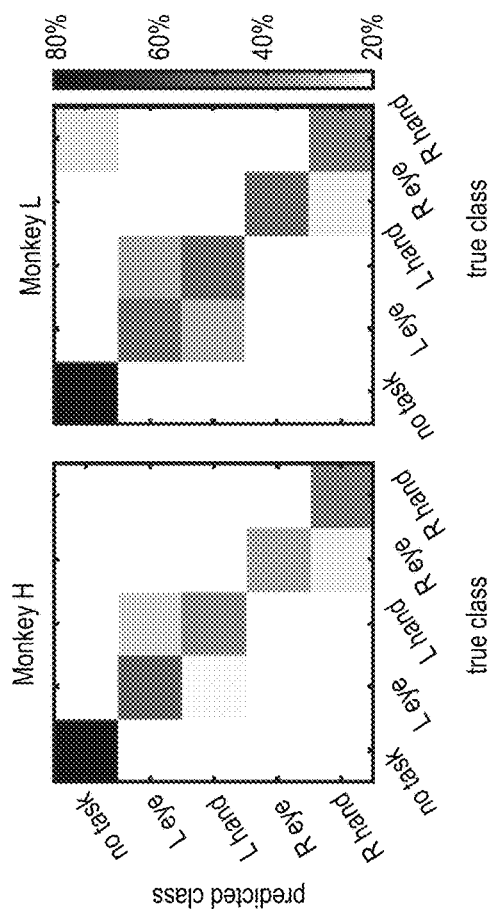
Figure 10C:
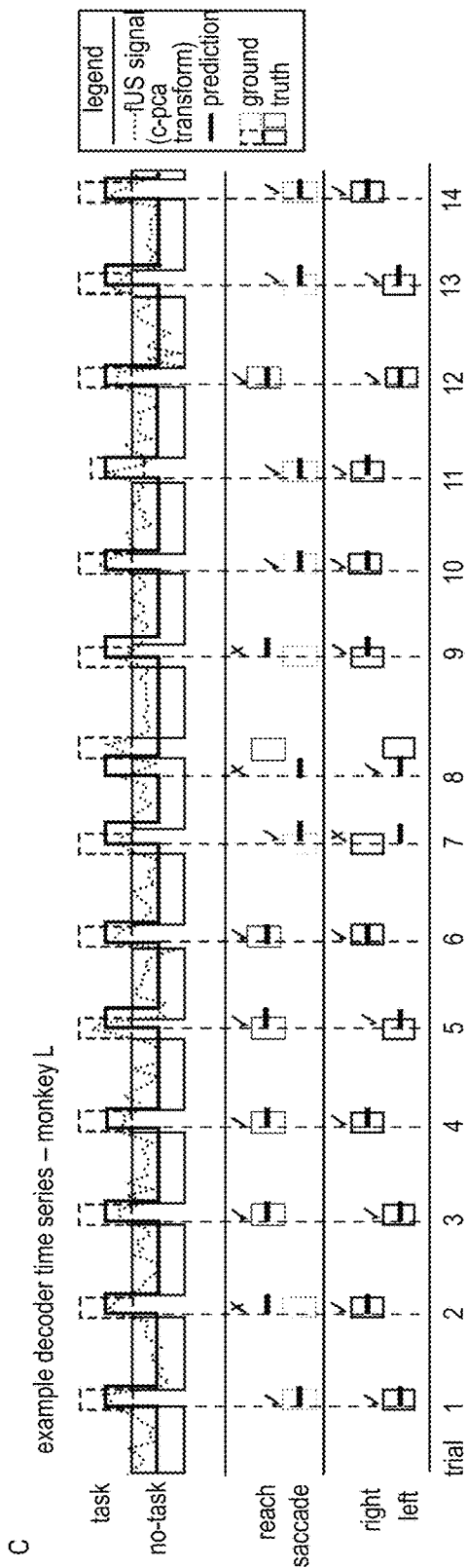

FIGS. 10A-10C depict decoding task, effector, and direction simultaneously. FIG. 10A shows intermingled memory-delayed saccade and reach task. A trial started with the animals fixating their gaze (and moving the joystick to) a central cue. The center fixation cue was either colored blue to cue saccades (top row) or red to cue reaches (bottom row), randomized trial by trial (i.e., not blocked). Next, a target (white circle) was flashed on either the left or right visual field. The animals had to remember its location while continuing to fixate their eye and hand on the center cue. When the center was extinguished (go signal), the animals performed a movement of either the eye or hand to the remembered peripheral target location. *Mean values across sessions shown; the fixation period was consistent within each session but varied across sessions from 2.4 to 4.3 s. FIG. 10B shows confusion matrices of decoding accuracy represented as percentage (columns add to 100%).

FIG. 10C shows example classification of 14 consecutive trials. Classification predictions are shown as lines. An example of the fUS image time series transformed by the classifier subspace appears in red. After predicting the task period, the classifier decoded effector (second row) and movement direction (third row) using data only from the predicted task period (first row). To demonstrate the ability of fUS to decode multiple dimensions of behavior from a single trial of data, the same two animals were trained to perform a memory-delayed, intermingled effectors task. This task was similar to the saccade and reach tasks in its temporal structure. However, in addition to the animals fixating their gaze during the fixation period, they also moved a we collected 1,576 trials (831 from monkey H and 745 from mon-key L) over four sessions (two from each animal) while they per-formed this task.

The temporal course of (1) the task structure, (2) the effector, and (3) the target direction of the animal were decoded using a decision tree decoder. First, the task memory periods were predicted versus non-memory periods (including movement, inter-trial interval, and fixation). This distinction is referred to as task/no task (FIG. 10C, task/no task). To predict when the monkey entered the memory period, the decoder used continuous data where each power Doppler image was labeled as task or no task. After predicting the animal entered the task phase, the second layer of the decision tree used data from the predicted task phase period to classify effector and direction (FIG. 10C, reach/saccade, left/right). Each of these decodes used the same strategy as before (cross-validated CPCA). FIG. 10B depicts the confusion matrix of decoding accuracy for each class for monkeys H and L. The classifier correctly predicted no-task periods 85.9% and 88.8% of the time for monkeys H and L, respectively, left versus right on 72.8% and 81.5% of trials for monkeys H and L, and eye versus hand on 65.3% and 62.1% of trials for monkeys H and L. All three decodes were significantly above chance level ($p<0.05$, binomial test versus chance, Bonferroni corrected for three comparisons).

Vascular Signal and Information Content

Figure 11A:
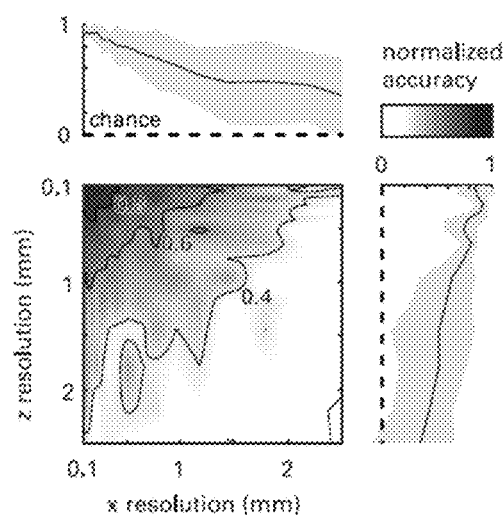
FIGS. 11A-11C show effects of spatial resolution, time window, and mean power Doppler intensity, according to an embodiment of the disclosure.
Figure 11B:
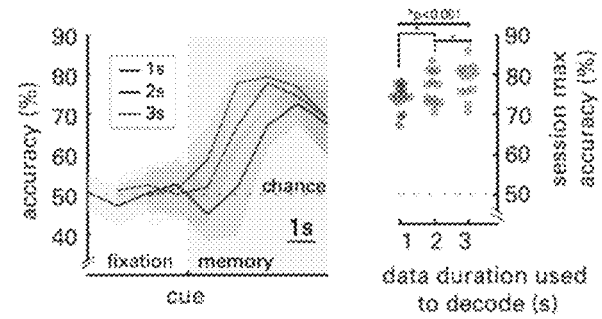
Figure 11C:
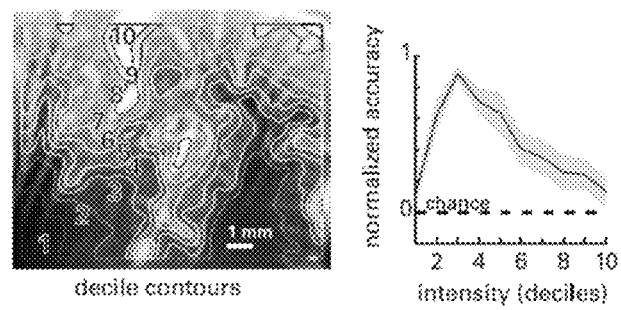

FIGS. 11A-11C show effects of spatial resolution, time window, and mean power Doppler intensity. In particular, FIG. 11A shows accuracy decreases with resolution in both the x direction (across the imaging plane) and z direction (depth in the plane) in an isotropic manner. As image resolution is directly proportional to the transmission frequency of the ultrasound probe, decoding accuracy may be improved by increasing transmission frequency of the ultrasound probe. Accordingly, hemodynamic changes may be imaged by utilizing high frequency ultrasound probes in order to improve spatial and/or temporal resolution. In one example, fUS images may be acquired with ultrasonic emissions at least 15 MHz.

FIG. 11B shows decoding accuracy as a function of decoder time bin durations (1-, 2-, and 3-s bins represented by black, red, and purple, respectively). Data are aligned to the end of the time bin used for decoding. Dots represent maximum decoder accuracy for each session for each of the bin sizes. Stars indicate statistical significance between groups (Student's t test, $p<0.001$ for all combinations). FIG. 11C shows a vascular map overlaid with contours dividing the image into deciles of mean power Doppler intensity. Decoding accuracy is shown as a function of the mean power Doppler intensity. Information content is greatest in quantile 3, which mostly contains small vasculature within the cortex. Subcortical and primary unit vasculature (i.e., deciles 1 and 10) are least informative to decoding movement direction.

All data represent means, and thinner lines, when present, represent standard error (SEM) across sessions. The purported benefits of fUS compared to established neuroimaging techniques include increased resolution and sensitivity. To test the benefit of increased resolution, movement goals were classified while systematically decreasing the resolution of the image. The images were resized using a low-pass filter in each of the dimensions of the imaging plane, x (across the probe surface) and z (with image depth). The entire image (where the downsized images contained fewer pixels) was then used to decode movement direction. Accuracy continuously decreased as voxel sizes increased (FIG. 11A). This effect was isotropic (i.e., similar for both x and z directions).

In order to determine if functional information useful for decoding would primarily be located in subresolution (<100 mm) vessels within the imaging plane, voxels were rank ordered by their mean power Doppler intensity and segmented them by deciles, resulting in a spatial map of ranked deciles (FIG. 11C). Deciles 1-2 mostly captured subcortical areas. Deciles 3-8 mostly captured cortical layers. Deciles 9 and 10 were largely restricted to large arteries, commonly on the cortical surface and in the sulci. Movement goals were then classified using data from each decile. Accuracy for each session was normalized, where 0 represents chance level (50%) and 1 represents the maximum accuracy reached across deciles. Accuracy peaked when the regions of the image within the third decile of mean Doppler power were used to decode movement direction. This decile was mostly represented by cortex vasculature, much of which is at or below the limits of fUS resolution. This shows that functional hyperemia arises from subresolution vessels and agrees with previous studies in rodents and ferrets.

Figure 12A:
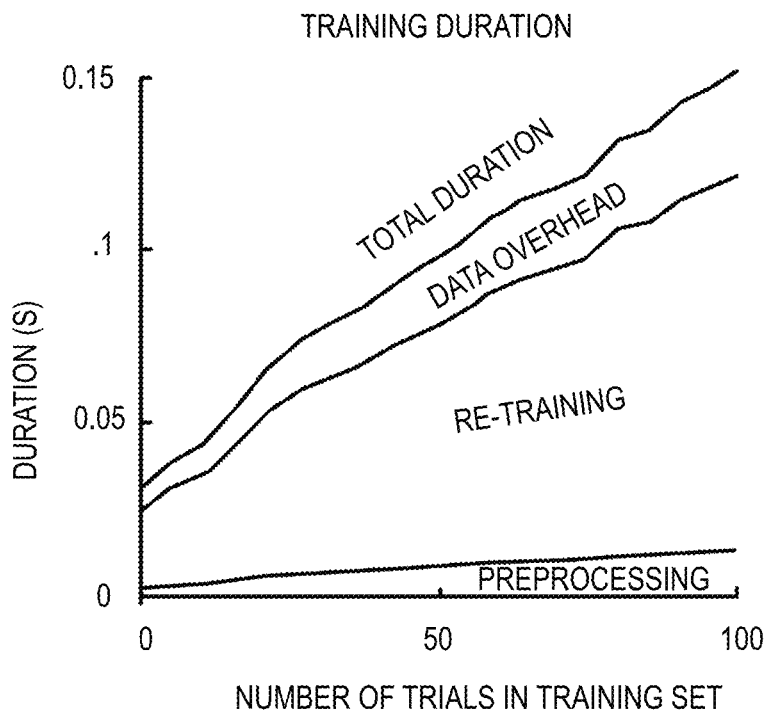
FIGS. 12A and 12B show real-time decoder timing, according to an embodiment of the disclosure.
Figure 12B:
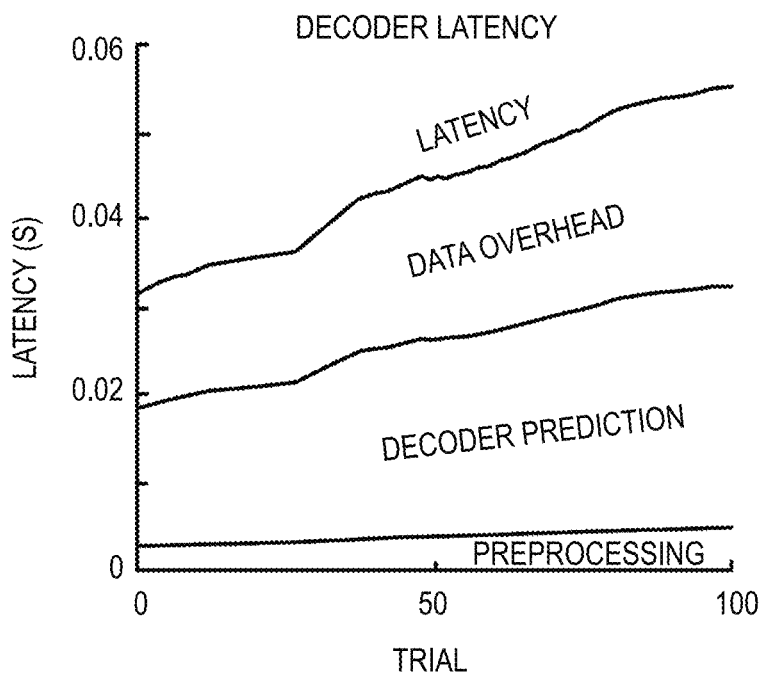

FIGS. 12A and 12B show real time decoder timing. In particular, FIG. 12A shows time required to train or re-train the classifier as a function of the number of trials in the training set. Duration is further divided into its major processes: preprocessing, training or re-training, and data overhead. FIG. 12B shows time required to predict a behavioral variable for a single trial as a function of the trial number (decoder latency). The decoder latency is further divided into preprocessing, decoder prediction, and data overhead. These data were acquired on a standard desktop PC using a single processing core of an Intel core i7-7700k at 3.60 GHz. Parallel processing methods could further decrease latencies.

The contributions presented here required significant advancements in large-scale recording of hemodynamic activity with single-trial sensitivity. Decoding capabilities are competitive with existing and mature techniques, establishing fUS as a technique for neuroscientific investigation in task paradigms that require single-trial analysis, real-time neurofeedback, or BMI. Although the neurophysiology presented here is in NHPs, the methods described may be expected to transfer well to human neuroimaging, single-trial decoding, and BMI.

Method Details

Animal Preparation and Implant

Two adult male rhesus macaques (*Macaca mulatta*) were implanted with polyether ether ketone head caps anchored to the skull with titanium screws. Then a custom polyether ketone (Monkey H) or stainless-steel (Monkey L) head holder was placed on the midline anterior aspect of the cap. Finally, a unilateral square chamber of 2.4 cm inner diameter, made of polyetherimide (Monkey H) or nylon (Monkey L) was placed over a craniotomy above the left intraparietal sulcus. The dura underneath the craniotomy was left intact. To guide the placement of the chamber, high-resolution (700 mm) anatomical MRI images were acquired before the surgery using a Siemens 3T MR scanner, with fiducial markers to register the animals' brains to stereotaxic coordinates.

Behavioral Setup

During each recording session, the monkeys were placed in a dark anechoic room. They sat in a custom designed primate chair, head fixed, facing an LCD monitor ~30 cm away. Visual stimuli were presented using custom Python software based on PsychoPy. Eye position was monitored at 60 Hz using a miniature infrared camera (Resonance Technology, Northridge, CA, USA) and ViewPoint pupil-tracking software (Arrington Research, Scottsdale, AZ, USA). Reaches were performed using a 2-dimensional joystick (Measurement Systems). Both eye and cursor positions were recorded simultaneously with the stimulus and timing information and stored for offline access. Data analysis was performed in MATLAB 2020a (MathWorks, Natick, MA, USA) using standard desktop computers.

Behavioral Tasks

The animals performed memory-guided eye movements to peripheral targets (FIG. 7A). Each trial started with a fixation cue (red diamond; 1.5 cm side length) presented in the center of screen (fixation period). The animal fixated for 5.35-6.33 s depending on training (mean 5.74 s across sessions). Then, a single cue (red diamond; 1.5 cm side length) appeared either on the left or the right hemifield for 200 ms, indicating the location of the target. Both targets were located equidistantly from the central fixation cue (230 eccentricity). After the cue offset, the animals were required to remember the location of the targets while maintaining eye fixation (memory period). This period was chosen to be sufficiently long to capture hemodynamic transients. The memory period was consistent within each session but varied across sessions from 4.02-5.08 s (mean 4.43 s across session) depending on the animal's level of training. Once the central fixation cue disappeared (i.e., go signal) the animals performed a direct eye movement (saccade) within 500 ms to the remembered location of the target. If the eye position arrived within a radius of 5° of the targets, it was re-illuminated and stayed on for the duration of the hold period (1 s). If the animal broke eye fixation before the go signal (i.e., shifted their gaze outsize of a window of 7.5 cm, corresponding to 14° of visual angle) the trial was aborted. Successful trials were followed by a liquid reward. The fixation and memory periods were subject to 400 ms of jitter sampled from a uniform distribution to preclude the animal from anticipating the change(s) of the trial phase.

Both animals also performed memory-guided reach movements to peripheral targets using a 2-dimensional joystick positioned in front of the chair with the handle at knee level. Each trial started with two fixation cues presented at the center of the screen. The animal fixated his eyes on the red diamond cue (1.5 cm side length) and acquired the green cue by moving a square cursor (0.3 cm side length) controlled by his right hand on the joystick (fixation period). The animal fixated for 2.53-5.85 s depending on training (mean 3.94 s across sessions). Then, a single green target (1.5 cm side length) was presented either on the left or the right visual field for a short period of time (300 ms). After the cue offset, the animal was required to remember the location of the targets for a memory period while maintaining eye and hand fixation. The memory period was consistent within each session but varied across sessions from 3.23-5.20 (mean 4.25 s across session). Once the central green cue disappeared, the animal performed a direct reach to the remembered target location within 500 ms, without breaking eye fixation. If they moved the cursor to the correct goal location, the target was re-illuminated and stayed on for duration of the hold period (1 s). Targets were placed at the same locations as in saccade trials. If the cursor moved out of the target location, the target was extinguished, and the trial was aborted. Any trial in which the animal broke eye fixation or initiated a reaching movement before the go signal or failed to arrive at the target location was aborted. Successful trials were followed with the same liquid reward as in saccade trials. The fixation and memory periods were subject to 400 ms of jitter sampled from a uniform distribution to preclude the animal from anticipating the change(s) of the trial phase.

Both animals were also trained on a task that intermingled memory delayed saccades and reaches (FIG. 10A). Similar to the reach task, each trial started with two fixation cues presented at the center of the screen: one for his eyes and one for his right hand. The target sizes were maintained from the reach task. The key difference was that the color of the gaze fixation diamond was randomized as blue or red: blue to cue saccades and red to cue reaches. After a 4.3 s memory period, a single white target (1.5 cm side length) was presented either on the left or right visual field for a short period of time (300 ms). After the cue offset, the animal was required to remember the location of the targets for the duration of the memory period. The memory period across all sessions for both monkeys was 4.0 s. Once the central green cue disappeared, the animal performed a saccade or reach via joystick to the remembered target location within 500 ms, without breaking fixation of the non-cued effector. If they moved the cursor to the correct goal location, the target was re-illuminated and stayed on for the duration of the hold period (1 s). If the cued effector moved out of the target location, the target was extinguished, and the trial was aborted. Any trial in which the animal broke fixation of the non-cued effector or initiated a movement of the cued effector before the go signal or failed to arrive at the target location was aborted. Successful trials were followed with the same liquid reward as in saccade and reach trials. The fixation and memory periods were subject to 400 ms of jitter sampled from a uniform distribution to preclude the animal from anticipating the change(s) of the trial phase.

Functional Ultrasound Sequence and Recording

During each recording session the ultrasound probe (128 elements linear array probe, 15.6 MHz center frequency, 0.1 mm pitch, Vermon, France) was placed in the chamber with acoustic coupling gel. This enabled us to acquire images from the posterior parietal cortex (PPC) with an aperture of 12.8 mm and depths up to 23 mm (results presented here show up to 16 mm depth). This large field of view allowed imaging several PPC regions simultaneously. These superficial and deep cortical regions included, but were not limited to, area 5d, lateral intraparietal (LIP) area, medial intraparietal (MIP) area, medial parietal area (MP), and ventral intraparietal (VIP) area.

A programmable high-framerate ultrasound scanner (Vantage 128 by Verasonics, Kirkland, WA) was used to drive a 128-element 15 MHz probe and collect the pulse echo radiofrequency data. A plane-wave imaging sequence was acquired at a pulse repetition frequency of 7500 Hz. We transmitted plane waves at tilted angles of −6° to +6° in 3° increments. Then, data originating from each angle as compounded to obtain one high-contrast B-mode ultrasound image. Each high-contrast B-mode image was formed in 2 ms, i.e., at a 500 Hz framerate.

Regional changes in cerebral flood volume induced by neurovascular coupling can be captured by ultrafast power Doppler ultra-sound imaging. Further, an ultrafast power Doppler sequence using a spatiotemporal clutter-filter was implemented to separate blood echoes from tissue backscattering. Power Doppler images of the NHP brain were generated using 250 compounded B-mode images collected over 0.5 s. Image formation and data storage were performed after the pulse sequence and took ~0.5 s. Thus, the pulse sequence and image formation/save resulted in power Doppler functional mapping of the NHP brain at a 1 Hz refresh rate.

Anatomical PPC regions were spatially located by their stereotaxic positions from the pre-surgical MRI. Response of these functional areas was confirmed by mapping activated voxels obtained during the experimental phase of this work. If necessary, the imaging plane was adjusted to record the most responsive area. Each acquisition consisted of 900-3600 blocks of 250 frames where each block represented 1 s of data (equivalent to 15-60 minutes runtime). Finally, we stored the in-phase and quadrature sampled data to high-speed solid-state drive memory for offline processing.

Power Doppler Image Processing

Singular value decomposition (SVD) to discriminate red blood cell motion from tissue motion and extracted the Doppler signal in each ensemble of 250 coherently compounded frames. The resulting images were then stored in a 3D array of 2D images in time series. In some experiments, motion of the entire imaging frame was observed. These shifts were indicative of a change in the position of the probe/tissue interface due to uncommonly forceful movements of the animal. These events were corrected using rigid-body image registration based on the open source NoRMCorre package using an empirical template created from the first 20 frames from the same session. We also tested non-rigid image registration but found little improvement, confirming that motion observed was due to small movements between the probe/dura interface rather than changes in temperature or brain morphology.

ERA Waveforms and Statistical Parametric Maps

Event-related average (ERA) waveforms (FIGS. 7C-7F, 7H, 7I, 8C, 8D, 8F, and 8G) of power Doppler change as percent-age change from baseline. The baseline consists of the three seconds preceding the first Doppler image obtained after the directional cue was given on any given trial. ERA waveforms are represented as a solid line with surrounding thinner lines representing the mean and standard deviation. Activation maps (FIGS. 7B, 7G, 8B, and 8E) by performing a one-sided t test for each voxel individually with false discovery rate (FDR) correction based on the number of voxels tested. In this test, the area under the curve of the change in power Doppler were compared during the memory phase of the event-related response. The movement direction represented the two conditions to be compared, and each trial represented one sample for each condition. A one-sided test was chosen because our hypothesis was that contralateral movement planning would elicit greater hemodynamic responses in LIP compared to ipsilateral planning (based on canonical LIP function). This has the added benefit of being easily interpretable: areas of activation represent contralateral tuning. Voxels with values of p<0.01 are displayed as a heatmap overlaid on a background vascular map for anatomical reference.

Single Trial Decoding

Decoding single trial movement intention involved three parts: 1) aligning CBV image time series with behavioral labels, 2) feature selection, dimensionality reduction and class discrimination, and 3) cross validation and performance evaluation. First, the imaging dataset was divided into event aligned responses for each trial, i.e., 2D Power Doppler images through time for each trial. The trials were then separated into a training set and testing set according to a 10-fold cross validation scheme. The training set was attached to class labels that represented the behavioral variable being decoded. For example, movement direction would be labeled left or right. The test set was stripped of such labels. Features were selected in the training set by ranking each voxel's q-value comparing the memory phase responses to target direction in the training data. Direction-tuned voxels (FDR corrected for number of pixels in image, q<0.05) of up to 10% of the total image were kept as features. For the intermingled effector task, all features were used (i.e., the whole image) because it did not require combining multiple t-maps. For dimensionality reduction and class separation, we used classwise principal component analysis (CPCA) and linear discriminant analysis (LDA), respectively. CPCA computes the principal components (PCs) in a piecewise manner individually for training data of each class. Principal components were retained to account for >95% of variance. Class separability was improved by running linear discriminant analysis (LDA) on the CPCA-transformed data. Mathematically the transformed feature for each trial can be represented by $f=T_{LDA}\Phi_{CPCA}(d)$, where $d\in R$ are the flattened imaging data for a single trial, $\Phi_{CPCA}$ is the piecewise linear CPCA transformation, and $T_{LDA}$ is the LDA transformation. $\Phi_{CPCA}$ is physically related to space and time and thus can be viewed within the context of physiological meaning (FIG. 9D). Subsequently used Bayes rule was used to calculate the posterior probabilities of each class given the observed feature space. Because $\Phi_{CPCA}$ is a piecewise function, this is done twice, once for each class, resulting in four posterior likelihoods: $P_L(L|f^*)$; $P_L(R|f^*)$; $P_R(L|f^*)$; $P_R(R|f^*)$, where $f^*$ represents the observation, $P_L$ and $P_R$ represent the posterior probabilities in the CPCA subspaces created with training data from left-directed and right-directed trials, respectively. Finally, the optimal PC vectors were stored and corresponding discriminant hyperplane from the subspace with the highest posterior probability. These findings were then used to predict the behavioral variable of interest for each trial in the testing set. That is, $f^*$ from fUS imaging data was computed for each trial in the testing set to predict the upcoming movement direction. Finally, the training and testing sets were rotated according to k-fold validation, storing the BMI performance metrics for each iteration. The mean decoding accuracy is shown as a percentage of correctly predicted trials (FIG. 9B). In measures across multiple sessions where an independent variable is being tested (e.g., number of trials in training set), a normalized accuracy was used that is linearly scaled to [0, 1] where 0 is chance level (50%) and 1 is the maximum accuracy across the set of values used in the independent variable (e.g., FIG. 9B). This was necessary to regularize raw accuracy values across multiple sessions and animals.

Analysis of Training Set Sample Size

As BMI models increase in complexity, their need for data also increases. To demonstrate the robustness of our piecewise linear decoding scheme to limited data, the amount of data used was systematically reduced in the training set (FIG. 9B). N−i trials were used in the training set and i trials in the testing set in a cross-validated manner, rotating the training/testing set i times for i=1, 2, . . . N−10. At N−10 because accuracy was diminished to chance level and when less than 10 trials are used in the training set, it becomes increasingly likely that there will be an under- or non-represented class, i.e., few or no trials to one of the movement directions. The mean normalized accuracy standard error of the means (SEM) across both animals and all recording sessions is shown as a function of the number of trials in the training set (N−i)(FIG. 9B).

Multicoder for Intermingled Effectors Task

For the intermingled effectors task (FIGS. 10A-C), the same decoding scheme was described above to decode effector and direction. However, instead of using data from the period defined by the experiment, a decision tree to define the task period was used. That is, we first predicted the memory period from the non-memory periods (i.e., task epoch versus no-task epoch). To do this, each frame of fUS in the training set was labelled with a label for task or no-task. Each frame was then decoded in the testing set using the same decoding scheme described above. The primary difference of note here is that individual frames of data were used rather than cumulative frames from within a known task period. We then refined these predictions by assuming that any time the classifier predicted the animal had entered a task state, they would be in that task state for three seconds. This allowed us to use three seconds' worth of data to train and decode the effector and direction variables. Note that while the task/no-task classifier makes a prediction every 1 s, the effector and direction make a prediction for each trial defined by the task/no-task classifier.

Cross Temporal Decoding

An analysis to determine the nature of hemodynamic encoding in PPC using a cross-temporal decoding technique was also performed. In this analysis, all temporal combinations of training and testing data were used, using a one second sliding window. 1 s of data was used from all trials to train the decoder and then attempted to decode from each of the 1 s windows of testing data throughout the trial. Then the training window was updated, and the process was repeated. This analysis results in an n×n array of accuracy values where n is the number of time windows in the trial. 10-fold cross-validated accuracies are shown as a percentage of correctly predicted trials (FIG. 9C). To assess the statistical significance of these results, a Bonferroni corrected binomial test versus chance level (0.5) was used where the number of comparisons was $n^2$. We overlaid a contour at p=0.05 to indicate the temporal boundaries of significant decoding accuracies.

Decoding with Reduced Spatial Resolution

Part of the motivation for using fUS is its spatial resolution. To test the effects of increased resolution, we synthetically reduced the resolution of the in-plane imaging data using a Gaussian filter. We performed this analysis at all combinations of x and z direction (width and depth, respectively) starting at true resolution (i.e., 100 μm) up to a worst-case of 5 mm resolution. The 10-fold cross-validated accuracy values were reported as a function of these decreasing resolutions as a 2D heatmap and as 1D curves of mean accuracy in both the x and z directions with shaded areas representing s.e.m. (FIG. 11A). As the out-of-plane dimension cannot be downsampled, the reported accuracy values are likely higher than those attainable by a technique with isotropic voxel size, e.g., fMRI.

Decoding with Different Time Windows

To analyze the effect of cumulative versus fixed length decoders, different sliding windows of data were used (1 s, 2 s, 3 s) to decode upcoming movement direction (left or right) using data from the memory delay period. These results are shown using accuracy as a function of trial time and the maximum accuracy achieved during the memory period for each session (FIG. 11B). Accuracies are represented at each time point through the fixation and memory periods using data aligned to the end of the time bin used for decoding. For example, an accuracy at t=3 s for a decoder using 3 s of data represents a result trained on data from t=0-3 s. To assess significance between different conditions, a student's two-tailed t test was used.

Power Doppler Quantiles

The source of hemodynamic information content was investigated by segmenting the images according to their mean power Doppler signal as a proxy for mean cerebral blood flow within a given area. Specifically, the image was segmented into deciles by mean power Doppler signal within a session, where higher deciles represented higher power and thus higher mean blood flow (FIG. 11C). Deciles were delineated by the number of voxels, i.e., the number of voxels was the same within each segment and did not overlap. Using only the voxels within each decile segment, the mean accuracy for each recording session was computed. The mean normalized accuracy is shown across all recording sessions (FIG. 9C) where thinner lines represent SEM.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "control system" on data stored on one or more computer-readable storage devices or received from other sources.

The term "control system" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

Selected Embodiments

Although the above description and the attached claims disclose a number of embodiments of the present invention, other alternative aspects of the invention are disclosed in the following further embodiments.

Embodiment 1. A neural interface system comprising: at least one ultrasound transducer; a controller storing instructions in non-transitory memory that when executed cause the controller to: acquire, via the at least one ultrasound transducer, a plurality of ultrasound images; process the plurality of ultrasound images, in real-time, to determine one or more movement intentions; and adjust one or more actuators of a device, in real-time, according to the one or more movement intentions, the device communicatively coupled to the controller; wherein the at least one ultrasound transducer is positioned to image an area of a brain of a subject.

Embodiment 2. The neural interface system of claim 1, wherein the plurality of ultrasound images is acquired by transmitting a set of plane waves, each of the set of plane waves transmitted at a different angulation; and wherein the at least one ultrasound transducer is a high-frequency ultrasound transducer configured to emit ultrasonic waves above a threshold frequency.

Embodiment 3. The neural interface system of claim 1, wherein the one or more movement intentions includes a task phase of a cognitive state of the subject, the task phase occurring prior to imagining, attempting, or executing an intended movement.

Embodiment 4. The neural interface system of claim 1, wherein the one or more movement intentions includes an intended effector, an intended movement direction, and/or an intended action.

Embodiment 5. The neural interface system of claim 1, wherein the device is a prosthetic limb, an orthotic assistance device, functional electrical stimulation, or a computing device.

Embodiment 6. The neural interface system of claim 1, wherein process the plurality of ultrasound images, in real-time, to determine one or more movement intentions comprises determining changes in cerebral blood flow over a duration using the plurality of ultrasound images.

Embodiment 7. The neural interface system of claim 1, wherein process the plurality of ultrasound images, in real-time, to determine one or more movement intentions includes classify one or more of a task phase, a movement intention direction, and an intended effector according to a machine learning algorithm receiving the plurality of ultrasound images as input.

Embodiment 8. The neural interface system of claim 7, wherein the machine learning algorithm is trained to classify one or more of the task phase, the movement intention direction, and the intended effector simultaneously.

Embodiment 9. The neural interface system of claim 1, wherein the controller includes further instructions that when executed cause the controller to process the plurality of ultrasound images, in real-time, to determine one or more goals simultaneously.

Embodiment 10. The neural interface system of claim 1, wherein the controller includes further instructions that when executed cause the controller to: while adjusting the one or more actuators of the device, acquire, a next plurality of ultrasound images, and process the next plurality of ultrasound images to determine one or more subsequent movement intentions.

Embodiment 11. The neural interface system of claim 10, wherein the controller includes further instructions that when executed cause the controller to: responsive to completing adjustment of one or more actuators of the device according to the one or more movement intentions, further adjust the one or more actuators of the device according to the next movement intention.

Embodiment 12. A system comprising: one or more ultrasound transducers positioned to image an area of a brain of a subject; an ultrasound scanning unit comprising one or more processors, the one or more processors storing instructions in non-transitory memory that when executed cause the one or more processors to: acquire, via the one or more ultrasound transducers, a plurality of ultrasound images; process the plurality of ultrasound images, in real-time, to determine a cognitive state of the subject associated with a task phase; and responsive to determining the task phase, determine one or more movement intentions based on the plurality of ultrasound images.

Embodiment 13. The system of claim 12, wherein the one or more movement intentions includes an intended effector, an intended movement direction, and/or an intended action.

Embodiment 14. The system of claim 13, wherein the one or more movement intentions are determined simultaneously.

Embodiment 15. The system of claim 12, wherein process the plurality of ultrasound images, in real-time, to determine a task phase of a cognitive state of the subject comprises process the plurality of ultrasound images according to a trained machine learning algorithm, the trained machine learning algorithm based on class-wise principal component analysis (CPCA) and linear discriminant analysis (LDA).

Embodiment 16. The system of claim 12, wherein the area of the brain is sensorimotor cortical or sub-cortical motor brain areas.

Embodiment 17. The system of claim 12, wherein the area of the brain is posterior parietal cortex, primary motor cortex, and/or premotor cortex.

Embodiment 18. A method for a brain-machine interface, the method comprising: receiving a plurality of ultrasound images from an ultrasound probe, the ultrasound probe positioned to image an area of a brain; processing, the plurality of ultrasound images to output a set of functional images, the functional images showing cerebral blood flow changes in the area of the brain; and classifying, via a trained machine learning algorithm, one or more intended behaviors of the subject based on the set of functional images.

Embodiment 19. The method of claim 17, wherein classifying, via the trained machine learning algorithm, one or more intended behaviors of the subject based on the set of functional images comprises applying class-wise principal component analysis (CPCA) on the set of functional images to output a set of CPCA transformed features and performing linear discriminant analysis on the CPCA transformed features.

Embodiment 20. The method of claim 17, further comprising, generating an actuation signal according to the classified one or more intended behaviors and transmitting the actuation signal to a device to execute the one or more intended behaviors; and wherein the plurality of ultrasound images are generated by transmitting a set of plane waves, each of the set of plane waves transmitted at a different angulation.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A neural interface system comprising:
an ultrasound transducer;
a controller storing instructions in non-transitory memory that when executed cause the controller to:
acquire, via the at least one ultrasound transducer, a plurality of ultrasound images;
process the plurality of ultrasound images, in real-time, to determine a movement intention for actuating a device from the plurality of ultrasound images by classifying one or more of a task phase, a movement intention direction, and an intended effector according to a machine learning algorithm receiving the plurality of ultrasound images as input, wherein the machine learning algorithm is trained using a plurality of ultrasound images and corresponding ones of a task phase, a movement intention direction, and an intended effector; and
adjust an actuator a device, in real-time, according to the determined movement intention, the device communicatively coupled to the controller;
wherein the ultrasound transducer is positioned to image an area of a brain of a subject.

2. The neural interface system of claim 1, wherein the plurality of ultrasound images is acquired by transmitting a set of plane waves, each of the set of plane waves transmitted at a different angulation; and wherein the at least one ultrasound transducer is a high-frequency ultrasound transducer configured to emit ultrasonic waves above a threshold frequency.

3. The neural interface system of claim 1, wherein the one or more movement intentions includes a task phase of a cognitive state of the subject, the task phase occurring prior to imagining, attempting, or executing an intended movement.

4. The neural interface system of claim 1, wherein the one or more movement intentions includes an intended effector, an intended movement direction, and/or an intended action.

5. The neural interface system of claim 1, wherein the device is a prosthetic limb, an orthotic assistance device, functional electrical stimulation, or a computing device.

6. The neural interface system of claim 1, wherein the process the plurality of ultrasound images, in real-time, to determine a movement intention comprises determining changes in cerebral blood flow over a duration using the plurality of ultrasound images and matching the determined changes in cerebral blood flow to changes in cerebral blood flow corresponding to the movement intention.

7. The neural interface system of claim 1, wherein the machine learning algorithm is trained to classify one or more of the task phase, the movement intention direction, and the intended effector simultaneously.

8. The neural interface system of claim 1, wherein the controller includes further instructions that when executed cause the controller to process the plurality of ultrasound images, in real-time, to determine a goal associated with the movement intention, the goal including one of an information defining goal, a performance task goal, a target object goal, or a position goal.

9. The neural interface system of claim 1, wherein the controller includes further instructions that when executed cause the controller to: while adjusting the actuator of the device, acquire, a next plurality of ultrasound images, and process the next plurality of ultrasound images to determine a subsequent movement intentions.

10. The neural interface system of claim 9, wherein the controller includes further instructions that when executed cause the controller to: responsive to completing adjustment of the actuator of the device according to the movement intention, further adjust the actuator of the device according to the subsequent movement intention.

11. A system comprising:
an ultrasound transducer positioned to image an area of a brain of a subject;
an ultrasound scanning unit comprising a processor, the processor storing instructions in non-transitory memory that when executed cause the one or more processors to:
acquire, via the ultrasound transducer, a plurality of ultrasound images;
process the plurality of ultrasound images, in real-time, to determine a task phase associated with a cognitive state of the subject by processing the plurality of ultrasound images according to a trained machine learning algorithm, the trained machine learning algorithm based on class-wise principal component analysis (CPCA) and linear discriminant analysis (LDA), wherein the machine learning algorithm is trained from an input set of ultrasound images corresponding to a task phase of a cognitive state of a subject; and
responsive to determining the task phase, determine a movement intention occurring prior to onset of actual movement by the subject based on the plurality of ultrasound images.

12. The system of claim 11, wherein the movement intention includes an intended effector, an intended movement direction, and/or an intended action.

13. The system of claim 12, wherein the movement intention is one of a plurality of movement intentions determined by the phase task, and wherein the plurality of movement intentions are determined simultaneously.

14. The system of claim 11, wherein the area of the brain is sensorimotor cortical or sub-cortical motor brain areas.

15. The system of claim 11, wherein the area of the brain is posterior parietal cortex, primary motor cortex, and/or premotor cortex.

16. A method for operating a brain-machine interface, the method comprising:

receiving a plurality of ultrasound images from an ultrasound probe, the ultrasound probe positioned to image an area of a brain;

processing, the plurality of ultrasound images to output a set of functional images, the functional images showing cerebral blood flow changes in the area of the brain; and classifying, via a trained machine learning algorithm, an intended behavior occurring prior to the onset of the behavior of the subject based on cerebral blood flow changes determined from the set of functional images by applying class-wise principal component analysis (CPCA) on the set of functional images to output a set of CPCA transformed features and performing linear discriminant analysis on the CPCA transformed features.

17. The method of claim 16, further comprising generating an actuation signal according to the classified intended behavior and transmitting the actuation signal to a device to execute the intended behavior; and wherein the plurality of ultrasound images are generated by transmitting a set of plane waves, each of the set of plane waves transmitted at a different angulation.

\* \* \* \* \*